US011688512B2

(12) United States Patent
Barclay

(10) Patent No.: US 11,688,512 B2
(45) Date of Patent: Jun. 27, 2023

(54) DEVICES, SYSTEMS, AND METHODS FOR DETERMINING A USE OF UNITS IN MEDICAL PROCEDURES TO ESTABLISH EFFICIENCY AND ALTERNATE PRICING

(71) Applicant: Bard Peripheral Vascular, Inc., Tempe, AZ (US)

(72) Inventor: Ben Barclay, Tempe, AZ (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 0 days.

(21) Appl. No.: 17/637,702

(22) PCT Filed: Aug. 26, 2019

(86) PCT No.: PCT/US2019/048093
§ 371 (c)(1),
(2) Date: Feb. 23, 2022

(87) PCT Pub. No.: WO2021/040685
PCT Pub. Date: Mar. 4, 2021

(65) Prior Publication Data
US 2022/0270748 A1     Aug. 25, 2022

(51) Int. Cl.
*G16H 40/20* (2018.01)
*G06Q 30/0201* (2023.01)
(Continued)

(52) U.S. Cl.
CPC ......... *G16H 40/20* (2018.01); *G06Q 30/0206* (2013.01); *G06Q 30/0207* (2013.01); *G06Q 30/0283* (2013.01); *G06N 20/00* (2019.01)

(58) Field of Classification Search
CPC ............... G16H 40/20; G06Q 30/0206; G06Q 30/0207; G06Q 30/0283; G06N 20/00
See application file for complete search history.

(56) References Cited

U.S. PATENT DOCUMENTS

| 8,484,043 B2 | 7/2013 | Brookhart |
| 9,898,765 B1 | 2/2018 | Jones, II et al. |

(Continued)

FOREIGN PATENT DOCUMENTS

| CN | 107833621 A | 3/2018 |
| JP | 4846944 B2 * | 12/2011 |
| JP | 4846944 B2 | 12/2011 |

OTHER PUBLICATIONS

Paul, Douglas D. "One Model or Two? Considerations for High-Volume Activity-Based Costing." Cost Management 35.6: 10-15. Thomson Reuters (Tax & Accounting) Inc. ( (Year: 2012).*
(Continued)

*Primary Examiner* — Linh Giang Le
(74) *Attorney, Agent, or Firm* — Dinsmore & Shohl LLP

(57) ABSTRACT

Devices, systems, and methods for providing per-procedure pricing for a product are disclosed. A system includes a facility monitoring system having one or more data gathering devices collecting data pertaining to use of a plurality of units of the product over a period of time. The system also includes a product provider system communicatively coupled to the facility monitoring system and including a determination device that receives the data and determines a total average number of units per procedure for the product, the determination device including a machine learning component trained to determine an expected number of units per procedure and determine a plurality of pricing tiers that establish a price is used to calculate an adjusted per-procedure price for the product over the period of time, the determination device issuing a rebate if the adjusted per-procedure price is less than an upfront cost paid.

20 Claims, 20 Drawing Sheets

(51) Int. Cl.
*G06Q 30/0207* (2023.01)
*G06Q 30/0283* (2023.01)
*G06N 20/00* (2019.01)

(56) References Cited

U.S. PATENT DOCUMENTS

| | | |
|---|---|---|
| 2002/0120468 A1 | 8/2002 | Atallah |
| 2004/0122710 A1 | 6/2004 | Holte |
| 2005/0246189 A1 | 11/2005 | Monitzer et al. |
| 2007/0033071 A1 | 2/2007 | Schmieding |
| 2008/0091659 A1 | 4/2008 | McFaul |
| 2010/0161345 A1 | 6/2010 | Cain et al. |
| 2011/0055034 A1 | 3/2011 | Ferris et al. |
| 2011/0166883 A1 | 7/2011 | Palmer et al. |
| 2011/0288879 A1* | 11/2011 | Gice .................. G06Q 10/10 705/2 |
| 2014/0067406 A1 | 3/2014 | Hyatt et al. |
| 2015/0248729 A1 | 9/2015 | Angheloiu |

OTHER PUBLICATIONS

International Search Report and Written Opinion dated May 25, 2020 pertaining to PCT Application No. PCT/US2019/048093.
Office Action dated Jun. 22, 2022 pertaining to Canadian Patent Application No. 3,152,542.
Office Action dated Jan. 18, 2023, pertaining to Chinese Patent Application 2019801015077.
Extended European Search Report dated Mar. 20, 2023 for EP Application 19943144.6.
Examiner's Report dated Mar. 20, 2023 pertaining to Australian Patent Application 2019462994.

* cited by examiner

| 11:29 AM  Fri Aug 2 | | | .ıll 🗢 77%🔋 |
|---|---|---|---|
| < | Recent Case Entries | | Home |

Test Hospital 1

2204

2202

Report Timeframe
January 2019 ⌄

| Jan 30, 2019<br>Date of Service | 9465907340665<br>Case ID | 1<br>Product(s) | Iliac<br>Location(s) | ⟩ |
| Jan 27, 2019<br>Date of Service | 6208706513228<br>Case ID | 1<br>Product(s) | AV Access<br>Location(s) | ⟩ |
| Jan 25, 2019<br>Date of Service | 7609245797060<br>Case ID | 1<br>Product(s) | AV Access<br>Location(s) | ⟩ |
| Jan 24, 2019<br>Date of Service | 6806046918965<br>Case ID | 1<br>Product(s) | Iliac<br>Location(s) | ⟩ |
| Jan 22, 2019<br>Date of Service | 1404206114308<br>Case ID | 2<br>Product(s) | Iliac, AV Access<br>Location(s) | ⟩ |
| ○ Jan 19, 2019<br>Date of Service | 8742967784938<br>Case ID | 2<br>Product(s) | AV Access<br>Location(s) | ⟩ |
| Jan 15, 2019<br>Date of Service | 9350782334741<br>Case ID | 1<br>Product(s) | Iliac<br>Location(s) | ⟩ |
| Jan 14, 2019<br>Date of Service | 4173388303844<br>Case ID | 1<br>Product(s) | AV Access<br>Location(s) | ⟩ |
| Jan 05, 2019<br>Date of Service | 2820607107845<br>Case ID | 1<br>Product(s) | Iliac<br>Location(s) | ⟩ |
| Jan 04, 2019<br>Date of Service | 7003049884450<br>Case ID | 1<br>Product(s) | AV Access<br>Location(s) | ⟩ |
| Jan 04, 2019<br>Date of Service | 3154786223447<br>Case ID | 1<br>Product(s) | Iliac<br>Location(s) | ⟩ |

Admin | Reports
Financial | Procedure | Billing

Company
Sample Company

Start Month [01/2019]   End Month [06/2019]   Hospital [All ▾]

search   Download CSV

| Case ID | Account Name | Date of Service | Updated at | User Corrected Error | Physician Name | Location | Category | Family | Description | Quantity |
|---|---|---|---|---|---|---|---|---|---|---|
| Ben | Test Hospital 1 | 6/27/2019 | 6/27/2019 | yes | Ariel Johns | SFA/PP/BTK | DCB | Lutonix .035 | Lutonix .035 5mm x 80mm x 75cm | 1 |
| Ben | Test Hospital 1 | 6/27/2019 | 6/27/2019 | yes | Ariel Johns | SFA/PP/BTK | DCB | Lutonix .035 | Lutonix .035 6mm x 40mm x 130cm | 1 |
| deon | Test Hospital 1 | 6/26/2019 | 6/27/2019 | no | Ethan Beier | SFA/PP/BTK | DCB | Lutonix .035 | Lutonix .035 6mm x 60mm x 75cm | 2 |
| zxsfeyiv1245 | Test Hospital 1 | 6/26/2019 | 6/26/2019 | no | nor herlinger | | DCB | Lutonix .035 | Lutonix .035 4mm x 100mm x 75cm | 1 |
| zxsfeyiv1245 | Test Hospital 1 | 6/26/2019 | 6/26/2019 | no | nor herlinger | | DCB | Lutonix .035 | Lutonix .035 7mm x 40mm x 130cm | 2 |
| ABC123 | Test Hospital 1 | 4/15/2019 | 6/17/2019 | no | Francisco Konopelski | AV Access | DCB | Lutonix .035 | Lutonix .035 6mm x 60mm x 75cm | 1 |
| 6923336140659 | Test Hospital 3 | 5/13/2019 | 6/13/2019 | no | Chieko Fay | AV Access | DCB | Lutonix .035 | Lutonix .035 5mm x 40mm x 75cm | 2 |
| 3206534424153 | Test Hospital 5 | 1/8/2019 | 6/13/2019 | no | Dominick Bogan | AV Access | DCB | Lutonix .035 | Lutonix .035 7mm x 40mm x 130cm | 1 |
| 8461549102051 | Test Hospital 3 | 3/3/2019 | 6/13/2019 | no | Christopher Ratke | Iliac | DCB | Lutonix .035 | Lutonix .035 6mm x 80mm x 40cm | 1 |

FIG. 24

| Company / Contracts / Edit | | | | | |
|---|---|---|---|---|---|
| Billing Code | Emerald | Platinum | Gold | Silver | Bronze |
| 100 | 10.00 | 20.00 | 30.00 | 40.00 | 50.00 |
| 101 | 15.00 | 25.00 | 35.00 | 45.00 | 55.00 |
| 102 | 20.00 | 25.00 | 30.00 | 35.00 | 40.00 |

DEVICES, SYSTEMS, AND METHODS FOR DETERMINING A USE OF UNITS IN MEDICAL PROCEDURES TO ESTABLISH EFFICIENCY AND ALTERNATE PRICING

BACKGROUND

Field

The present specification generally relates to devices, systems, and methods for determining use of units of a product in a plurality of medical procedures and, more specifically, to devices, systems, and methods that provide cost-per-procedure-like pricing after receiving a price-per-unit payment up front based on the use of units of the product in the plurality of medical procedures.

Technical Background

Medical facilities, such as hospitals, doctor's offices, urgent care centers, outpatient surgical centers, and/or the like utilize a number of products when performing a procedure. Given the variability of certain procedures, any number of units may be used during a procedure. That is, a procedure on a first subject may use a single unit of a particular product, while the same procedure on a second subject may use a plurality of units of a particular product. This generally causes an issue with the administrators of a medical facility because certain procedures are billed at a per-procedure rate, yet the products are purchased at a rate per unit. As such, in the examples provided above, the procedure on the first subject is more cost effective and more profitable than the procedure on the second subject, which is known as procedural cost variability. Such variability also is detrimental to an overall cost predictability of a facility. That is, a facility may struggle to budget for future procedures because the cost per procedure varies.

Accordingly, there exists a need for facilities to move to a more fixed cost per procedure for the purposes of increasing profitability and improving overall cost predictability. However, such a move is not feasible without established devices, systems, and methods that generate a dataset and determine information from the dataset to provide a fixed cost per-procedure pricing scheme.

SUMMARY

In a first aspect, a system for providing per-procedure pricing for a product includes a facility monitoring system and a product provider system. The facility monitoring system includes one or more data gathering devices having one or more input/output hardware components and imaging device hardware. The one or more data gathering devices collect data pertaining to use of a plurality of units of the product over a period of time via the one or more input/output hardware components and the imaging device hardware. The product provider system is communicatively coupled to the facility monitoring system. The product provider system includes a determination device that receives the data from the one or more data gathering devices and determines a total average number of units per procedure for the product. The determination device includes a machine learning component trained to determine an expected number of units per procedure and determine a plurality of pricing tiers. The pricing tiers establishing a price that is used by the determination device to calculate an adjusted per-procedure price for the product over the period of time. The determining device issues a rebate if the adjusted per-procedure price is less than an upfront cost paid.

In a second aspect, a method of providing per-procedure pricing for a product by a determination device includes retrieving, by the determination device, historical use data for the product. The method further includes determining, by the determination device, a total average number of units per procedure for the product. The method further includes providing, by the determination device, the historical use data and the total average number of units per procedure to a machine learning component. The machine learning component generates a model from the historical use data and the total average number of units per procedure and determines an expected number of units per procedure based on the model. The method further includes determining, by the determination device, a plurality of pricing tiers for the price per procedure. The method further includes determining, by the determination device, a per-procedure pricing to be offered from the plurality of pricing tiers based on a determined efficiency of use of the product. The efficiency of use represents a closeness to the expected number of units per procedure. The method further includes calculating, by the determination device, an adjusted price to be paid based on the per-procedure pricing and a total number of procedures for a period of time. The method further includes issuing, by the determination device, a rebate when a total upfront cost paid for all units on a per-unit basis is greater than the adjusted price to be paid. The rebate represents a difference between the total upfront cost and the adjusted price to be paid.

In a third aspect, a determination device that provides per-procedure pricing for a product, the device including a processing device and a non-transitory, processor readable storage medium communicatively coupled to the processing device. The non-transitory, processor readable storage medium includes one or more programming instructions thereon that, when executed, cause the processing device to retrieve historical use data for the product, determine a total average number of units per procedure for the product, provide the historical use data and the total average number of units per procedure to a machine learning component, where the machine learning component generates a model from the historical use data and the total average number of units per procedure and determines an expected number of units per procedure based on the model, determine a plurality of pricing tiers for the price per procedure, determine a per-procedure pricing to be offered from the plurality of pricing tiers based on a determined efficiency of use of the product, where the efficiency of use represents a closeness to the expected number of units per procedure, calculate an adjusted price to be paid based on the per-procedure pricing and a total number of procedures for a period of time, and issue a rebate when a total upfront cost paid for all units on a per-unit basis is greater than the adjusted price to be paid. The rebate represents a difference between the total upfront cost and the adjusted price to be paid.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 15B schematically depicts a screen shot of an illustrative barcode interface according to one or more embodiments shown or described herein;

FIG. 16 schematically depicts a screen shot of an illustrative user interface depicting a record entry success according to one or more embodiments shown or described herein;

FIG. 20 schematically depicts a screen shot of an illustrative user interface including a date picker according to one or more embodiments shown or described herein;

FIG. 21 schematically depicts a screen shot of an illustrative user interface including a customizable financial report according to one or more embodiments shown or described herein;

FIG. 22 schematically depicts a screen shot of an illustrative user interface including a list of completed procedures according to one or more embodiments shown or described herein;

FIG. 24 schematically depicts a screen shot of an illustrative web based interface for viewing another summary of information according to one or more embodiments shown or described herein;

FIG. 26 schematically depicts a screen shot of an illustrative web based interface for viewing tiered pricing according to one or more embodiments shown or described herein;

DETAILED DESCRIPTION

Figure 1:
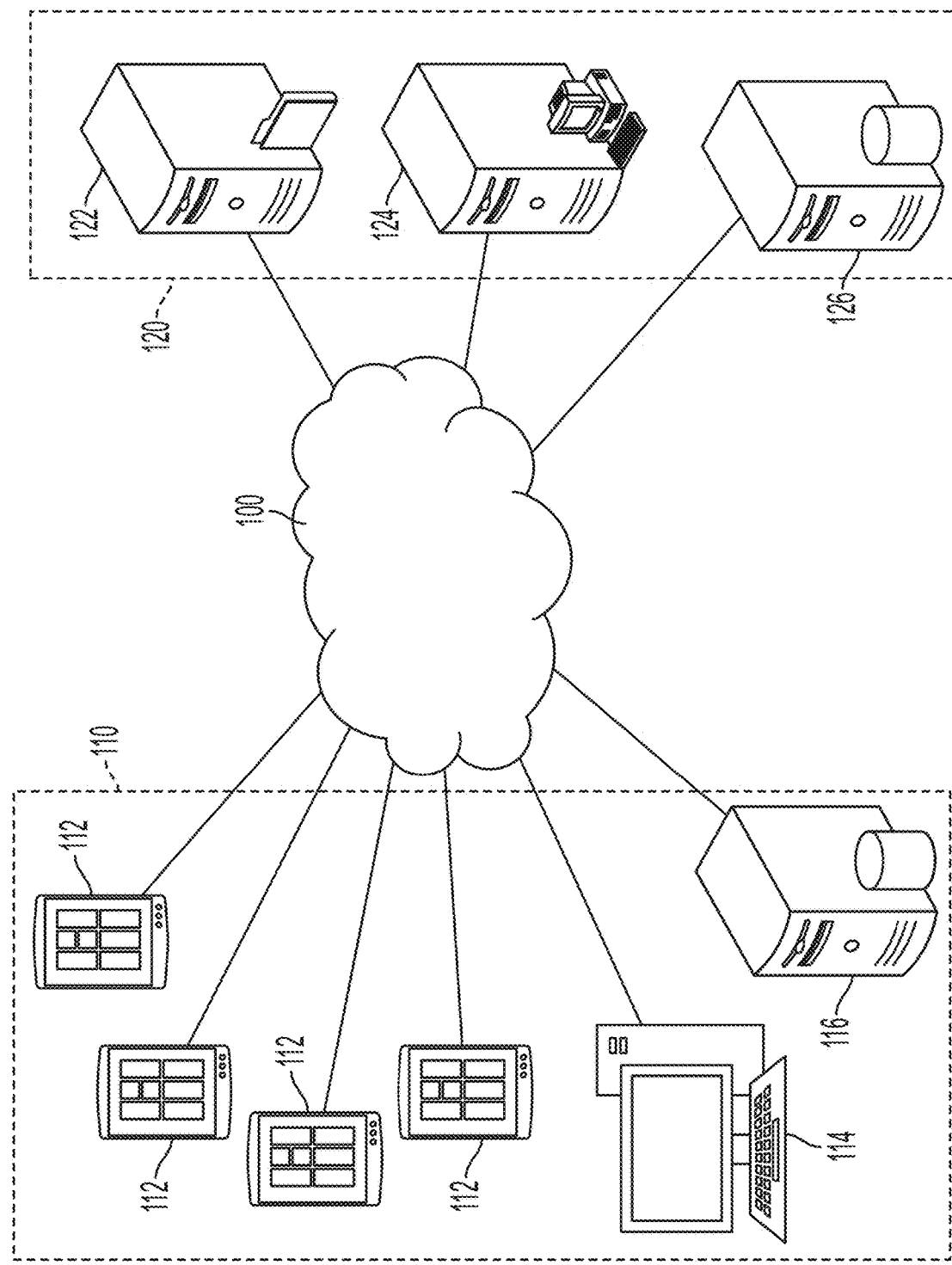
FIG. 1 schematically depicts a system including interconnectivity between a plurality of components in a facility monitoring system and a plurality of components in a product provider system in an illustrative data gathering network according to one or more embodiments shown or described herein.

Reference will now be made in detail to embodiments of devices, systems, and methods for determining a use of units of a product in a plurality of medical procedures and providing cost-per-procedure-like pricing after receiving a price-per-unit payment up front based on the determined use of units, examples of which are illustrated in the accompanying drawings. Whenever possible, the same reference numerals will be used throughout the drawings to refer to the same or like parts. One embodiment of a system for determining a use of units of a product in a plurality of medical procedures and providing cost-per-procedure-like pricing after receiving a price-per-unit payment up front based on the determined use of units is depicted in FIG. 1, in which the system includes a plurality of components in a facility monitoring system and a plurality of components in a product provider system, the facility monitoring system (and components thereof) being communicatively coupled to the product provider system (and components thereof) via a data gathering network. The components within the facility monitoring system include, but are not limited to, one or more data gathering devices, user interface device, and/or facility database server. The components within the product provider system include, but are not limited to, determination device, interface provider, and/or database server.

The phrase "communicatively coupled" is used herein to describe the interconnectivity of various components of the system for monitoring the positioning and the vital signs of a subject and means that the components are connected either through wires, optical fibers, or wirelessly such that electrical, optical, and/or electromagnetic signals may be exchanged between the components. It should be understood that other means of connecting the various components of the system not specifically described herein are included without departing from the scope of the present disclosure.

The devices, systems, and methods described herein are particularly arranged and configured in a particular manner to provide a medical facility with an ability to receive information from a products provider that is used by the medical facility to make strategic changes to the way the medical facility does business. The information provided to the medical facility is currently not obtainable by medical facilities due to the disparate data systems generally used by such medical facilities. For example, a single facility may include a clinical data system, a billing data system, and/or the like, none of which are configured to share information with one another (i.e., the systems are not integrated into a cohesive data set). As such, facilities cannot adequately make decisions due to these disparate data systems. The devices, systems, and methods described herein allow data logging at the time of each procedure, which is then used later on for the purposes of adjusting pricing and determining efficiency, as described in greater detail herein.

Referring now to the drawings, FIG. 1 depicts an illustrative network, generally designated 100, that communicatively couples a plurality of systems and/or devices to one another for the purposes of determining a use of units of a product in a plurality of medical procedures and providing cost-per-procedure-like pricing after receiving a price-per-unit payment up front based on the determined use of units according to embodiments shown and described herein. As illustrated in FIG. 1, the network 100 may include a wide area network (WAN), such as the internet, a local area network (LAN), a mobile communications network (MCN), a public service telephone network (PSTN) and/or other network and may be configured to electronically connect a facility monitoring system 110 and a product provider system 120. In addition, the network 100 is also configured to electronically connect various components of the facility monitoring system 110 and the product provider system 120. For example, the network 100 may connect one or more data gathering devices 112, a user interface device 114, and/or a facility database server 116 of the facility monitoring system and a determination device 122, an interface provider 124, and/or a database server 126 of the product provider system 120.

The facility monitoring system 110 is generally a plurality of components that function together to collect information pertaining to one or more procedures, various products used during each of the one or more procedures, a number of units used per product per procedure, and/or the like. The facility monitoring system 110 may also store the collected information and provide the collected information to a user via a user interface in a manner that allows a user to determine product and unit use, a cost per unit of a particular product, an average cost per procedure for a particular product, and/or the like, as described in greater detail herein. Illustrative components included in the facility monitoring system 110 include, but are not limited to, the one or more data gathering devices 112, the user interface device 114, and/or the facility database server 116.

The one or more data gathering devices 112 are generally computing devices that are maintained in or near an area where a procedure occurs in a facility. That is, each of the one or more data gathering devices 112 may be placed, installed, or the like in or adjacent to a procedure area, such as, for example, an operating room, a triage room, a cardiology procedure room, a control room in an MRI suite, a patient room, a hospital room, a room for subject-clinician interaction (e.g., a room where the clinician sees or treats the subject), and/or the like. In some embodiments, each of the one or more data gathering devices 112 may be placed adjacent to one or more other systems, devices, computers, and/or the like that are used for recording information pertaining to the procedure, monitoring the procedure, observing operation of machines used during the procedure and/or information provided by the machines used during the procedure, and/or the like. For example, if the procedure is an MRI procedure, one of the one or more data gathering devices 112 may be placed or installed in the MRI control room alongside the various other equipment that is included in the MRI control room. As described in greater detail herein, each of the one or more data gathering devices 112 may be arranged and configured for a user to input information pertaining to one or more products used during the procedure, as well as a number of units of each of the one or more products used. Each of the one or more data gathering devices 112 may be arranged and configured to allow for input before a procedure, during a procedure, or after a procedure, as described in greater detail herein. In some embodiments, each of the one or more data gathering devices 112 may be a commercially available product that has been particularly programmed to perform the processes described herein. For example, illustrative commercially available products may be, but are not limited to, an iPad® from Apple, Inc. (Cupertino, Calif.), a Surface® device from Microsoft Corporation (Redmond, Wash.), a Kindle® Fire® device from Amazon.com, Inc. (Seattle, Wash.), a Galaxy® Tab device from Samsung Electronics Co., Ltd. (Seol, South Korea), and/or the like.

While the embodiment of FIG. 1 depicts four of the data gathering devices 112, the number of data gathering devices 112 is not limited by the present disclosure. That is, less than four or greater than four data gathering devices 112 may be included within the facility monitoring system 110 in some embodiments. In some embodiments, the number of data gathering devices 112 may correspond to a number of procedure areas in a facility. That is, if a particular facility contains twenty five (25) procedure areas, the facility monitoring system 110 may include twenty five (25) data gathering devices 112, each of the data gathering devices 112 corresponding to each of the procedure areas.

The user interface device 114 is generally a device that provides information pertaining to the information collected by the data gathering devices 112 to a user within a facility. For example, the user interface device 114 may be usable to provide statistical information relating to various procedures to users such as facility administrators or the like. That is, the user interface device 114 may provide information pertaining to a total number of procedures, a total number of products and which products are used, a total number of units for a particular product, an average number of procedures, an average number of products, an average number of units for a particular product and/or a particular procedure, historical numbers (e.g., totals, averages, etc.), comparison of products, procedures, averages, medical personnel involved in procedures, and/or the like. In some embodiments, the user interface device 114 may provide an interface to facilitate a user's actions in purchasing products, budgeting, and/or the like. As such, a user of the user interface device 114 may view information pertaining to medical personnel, procedures, products, and units, determine procedure performance, purchase products, receive rebates, and/or the like, as described herein.

In some embodiments, the functionality provided by each of the one or more data gathering devices 112 and the functionality provided by the user interface device 114 may be combined into a single component. That is, a combined component may be used for the purposes of collecting information and may further be used to provide information pertaining to the information collected. In some embodiments, each of the one or more data gathering devices 112 may additionally contain the various components and functionality described herein with respect to the user interface device 114 to provide information to a user pertaining to the information that is collected.

In some embodiments, the data and/or information collected by the one or more data gathering devices 112 may not be stored locally on the one or more data gathering devices 112 (except for temporary files that may be used for a brief period of time before data and/or information is offloaded from the one or more data gathering devices 112). As such, the facility database server 116 is provided in the facility monitoring system 110. The facility database server 116 is generally a server computing device that is particularly configured to store data and/or information obtained from the one or more data gathering devices 112. In some embodiments, the facility database server 116 may further provide data and/or information to the one or more data gathering devices and/or the user interface device 114 when such data and/or information is requested (e.g., to review historical product use, historical units per procedure, and/or the like).

In some embodiments, the data and/or information collected by the one or more data gathering devices 112 may be offloaded to one or more components located in the product provider system 120, such as, for example, the database server 126. That is, the data and/or information collected by the one or more data gathering devices 112 may be stored by the facility database server 116 and/or the database server 126. In some embodiments, the facility database server 116 may be omitted such that the data and/or information collected by the one or more data gathering devices 112 is only stored by the database server 126.

The product provider system 120 is generally a plurality of components that function together to collect the information pertaining to one or more procedures, the various products used during each of the one or more procedures, the number of units used per product per procedure, and/or the like from the various components of the facility monitoring system 110 (e.g., the one or more data gathering devices), analyze the information, perform one or more machine learning processes with the information, provide information generated as a result of one or more machine learning processes, automatically determine pricing, provide pricing, and/or the like, as described in greater detail herein. Illustrative components included in the product provider system 120 include, but are not limited to, the determination device 122, the interface provider 124, and/or the database server 126.

The determination device 122 is generally a device that receives the collected data from one or more of the components of the facility monitoring system 110 (e.g., from the one or more data gathering devices 112), performs analytics on the data, executes one or more machine learning processes with the data, generates a machine learning model using the data, determines information pertaining to an average or expected number of units of a particular product per procedure, determines information pertaining to an expected efficiency of use of a particular product for a particular procedure, determines pricing based on determined information, and/or the like.

The interface provider 124 is generally a device that provides the information determined by the determination device 122 to a user in a user interface that allows the user to manipulate the information received, request additional information, make decisions, and/or the like. For example, the user interface device 114 may be usable to provide the results of machine learning processes for determining an expected number of units per procedure, the results of an expected efficiency, the results of a determined price based on the expected number of units and expected efficiency, and/or the like. That is, the user interface device 114 may be used to facilitate price setting for purchases of a particular product and/or for issuing rebates, as described in greater detail herein.

As described herein, the data and/or information collected by the one or more data gathering devices 112 may be stored on the database server 126 (either in lieu of the facility database server 116 or in addition to the facility database server 116). The database server 126 is generally a server computing device that is particularly configured to store data and/or information obtained from the one or more data gathering devices 112, as well as information generated by the determination device 122 and/or received from the interface provider 124. In some embodiments, the database server 126 may further provide data to the one or more data gathering devices 112, the user interface device 114, the determination device 122, and/or the interface provider 124 when such data is requested (e.g., to review historical product use, historical units per procedure, a determined expected amount of use, a determined efficiency, a determined price, and/or the like).

It should be understood that while the user interface device 114 is depicted in FIG. 1 as a personal computer and the facility database server 116, the determination device 122, the interface provider 124, and the database server 126 are depicted as servers, these are nonlimiting examples. More specifically, in some embodiments any type of computing device (e.g., mobile computing device, personal computer, server, etc.) may be utilized for any of these components. Additionally, while each of these devices is illustrated in FIG. 1 as a single piece of hardware, this is also merely an example. More specifically, each of the one or more data gathering devices 112, the user interface device 114, the facility database server 116, the determination device 122, the interface provider 124, and the database server 126 may represent a plurality of computers, servers, databases, or the like.

Figure 2:
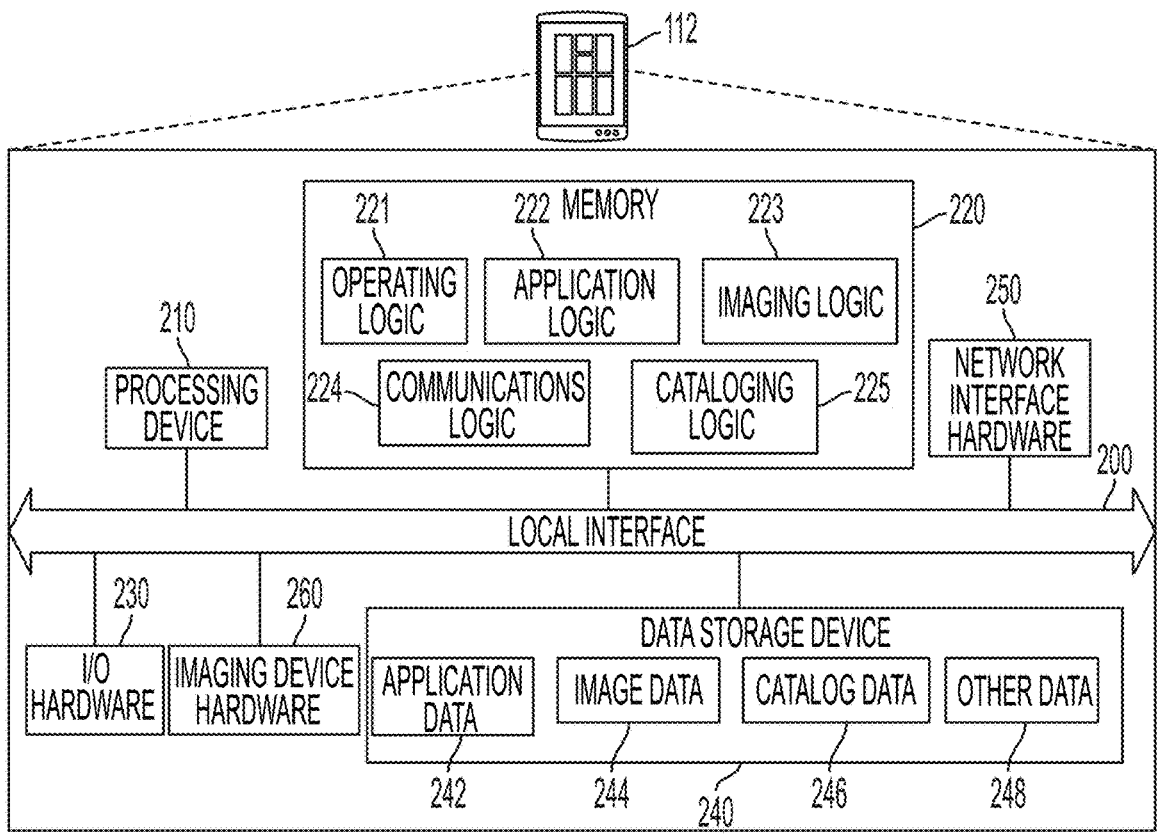
FIG. 2 schematically depicts a block diagram of illustrative internal components of a data gathering device in a facility monitoring system according to one or more embodiments shown or described herein.

Illustrative internal components of one of the one or more data gathering devices 112 are depicted in FIG. 2. The various internal components of the data gathering device 112 may provide functionality of the data gathering device 112, such as the functionality described herein. As depicted in FIG. 2, the data gathering device 112 may further include a local interface 200 (e.g., a bus) that communicatively interconnects the various components, including, but not limited to, a processing device 210, memory 220, input/output (I/O) hardware 230, a data storage device 240, network interface hardware 250, and/or imaging device hardware 260.

The processing device 210, such as a computer processing unit (CPU), may be the central processing unit of the data gathering device 112, performing calculations and logic operations required to execute a program. The processing device 210, alone or in conjunction with one or more of the other elements disclosed in FIG. 2, is an illustrative processing device, computing device, processor, or combination thereof, as such terms are used in this disclosure.

The memory 220, such as read only memory (ROM) and random access memory (RAM), may constitute illustrative memory devices (i.e., non-transitory, processor-readable storage media). Such memory 220 may include one or more programming instructions thereon that, when executed by the processing device 210, cause the processing device 210 to complete various processes, such as the processes described herein (e.g., processes described with respect to FIG. 8). Optionally, the program instructions may be stored on a tangible computer-readable medium such as a digital disk, flash memory, a memory card, a USB drive, an optical disc storage medium (e.g., Blu-ray™, CD, DVD), and/or other non-transitory, processor-readable storage media.

In some embodiments, the program instructions contained on the memory 220 may be embodied as a plurality of software modules, where each module provides programming instructions for completing one or more tasks. For example, as shown in FIG. 2, the memory 220 may contain one or more of operating logic 221, application logic 222, imaging logic 223, communications logic 224, and/or cataloging logic 225. The operating logic 221 may include programming instructions for an operating system and/or other software for managing components of the data gathering device 112 and/or providing a general user interface to a user.

The application logic 222 may include programming instructions for a software application that is configured to provide particular functionality within the operating system to a user. For example, the application logic 222 may include an "app" that is downloaded and installed onto the data gathering device 112, such as from an app store or the like. The application included in the application logic 222 may provide user-facing functionality for entering data pertaining to products, procedures, personnel, units, and/or the like. In some embodiments, the application may allow a user to activate the imaging device hardware 260 to capture an image of a particular product or portion thereof (e.g., a barcode located on product packaging or the like). In some embodiments, the application provided by the application logic 222 may include programming for allowing a user to view historical information, average or expected numbers, pricing, and/or the like. In some embodiments, the application provided by the application logic 222 may include programming for allowing a user to select data to be transmitted (e.g., transmitted to the facility database server 116, one or more components of the product provider system 120, and/or the like). In some embodiments, the application provided by the application logic 222 may include programming for allowing a user to select items for purchase.

The imaging logic 223 generally includes programming instructions for operating the imaging device hardware 260. That is, the programming instructions contained within the imaging logic 223 directing the imaging device hardware 260 to capture an image adjust various image sensor settings, adjust various optical settings, and/or the like. In some embodiments, the imaging logic 223 may include a commercially available software imaging program that obtains raw data from the imaging device hardware 260 and generates one or more images therefrom.

The communications logic 224 may generally include programming instructions for transmitting and/or receiving one or more signals to/from an external component via the I/O hardware 230 and/or the network interface hardware 250 (e.g., signals to/from one or more of the various components of the facility monitoring system 110 and/or one or more components of the product provider system 120 depicted in FIG. 1), transmitting and/or receiving data to/from an external component via the I/O hardware 230 and/or the network interface hardware 250 (e.g., signals to/from one or more of the various components of the facility monitoring system 110 and/or one or more components of the product provider system 120 depicted in FIG. 1), and/or the like. For example, the communications logic 224 may contain programming instructions for receiving electrical signals, extracting information from the electrical signals, and transmitting signals and/or data (e.g., data containing the information) via the I/O hardware 230 and/or the network interface hardware 250.

Still referring to FIG. 2, the cataloging logic 225 may generally include programming instructions for organizing information received via one or more user inputs (e.g., received through a user interface coupled to the I/O hardware 230 as described herein, information received via the network interface hardware 250, and/or information received from the imaging device hardware 260 (e.g., image data, raw data, and/or the like). For example, programming included in the cataloging logic 225 may organize image data received from the imaging device hardware 260 so that the image data is associated with a record that is used to catalog a particular product used for a procedure, as well as the number of units used for a particular procedure.

The I/O hardware 230 may communicate information between the local interface 200 and one or more external components that may be used during operation of the data gathering device 112. For example, the I/O hardware 230 may act as an interface between an external data storage device and other components of the data gathering device 112, so as to facilitate data transfer between the external data storage device and the data gathering device 112.

The network interface hardware 250 may generally provide the data gathering device 112 with an ability to interface with one or more components external to the data gathering device 112. For example, the network interface hardware 250 may be used to facilitate communication between the data gathering device 112 and one or more of the other components communicatively coupled to the network 100 depicted in FIG. 1. Still referring to FIG. 2, communication with external devices may occur using various communication ports (not shown). An illustrative communication port may be attached to a communications network, such as the Internet, an intranet, a local network, a direct connection, and/or the like. In some embodiments, the network interface hardware 250 may include any wired or wireless networking hardware, such as a modem, LAN port, wireless fidelity (Wi-Fi) card, WiMax card, Long Term Evolution (LTE) hardware, mobile communications hardware, and/or other hardware for communicating with other networks and/or devices. In some embodiments, the I/O hardware 230 and the network interface hardware 250 may be integrated into a single device that handles all communications to and from the data gathering device 112.

The data storage device 240, which may generally be a storage medium that is separate from the memory 220, may contain a data repository for storing electronic data. The data storage device 240 may be any physical storage medium, including, but not limited to, a hard disk drive (HDD), memory, removable storage, and/or the like. While the data storage device 240 is depicted as a local device in FIG. 2, it should be understood that the data storage device 240 may be a remote storage device that is remotely located from the data gathering device 112, such as, for example, a remote server computing device or the like.

Illustrative data that may be contained within the data storage device 240 may include, for example, application data 242, image data 244, catalog data 246, and/or other data 248. The application data 242 may be data that supports an application contained in the application logic 222, such as, for example, various repositories containing data pertaining to a user interface. The image data 244 generally includes data that is collected from the imaging device hardware 260, including, but not limited to, raw data generated as a result of operation of the imaging device hardware 260 and/or processed images that are generated as a result of operation of the imaging device hardware 260 and/or one or more logic modules of the memory 220. The catalog data 246 is data that is generated as a result of operation of the instructions contained within the cataloging logic 225. In some embodiments, the catalog data 246 may be temporary data pertaining to records of the various products, units, procedures, and personnel that are obtained by the data gathering device 112 before the data is offloaded to a data storage component, such as, for example, the facility database server 116 and/or the database server 126. The other data 248 is not limited by the present disclosure, and may generally be any other data that is generated and/or stored as a result of operation of the data gathering device 112 or component thereof.

The imaging device hardware 260 is coupled to the local interface 200 and is communicatively coupled to the processing device 210. The imaging device hardware 260 may be any device having one or more sensing devices (e.g., pixels) capable of detecting radiation. The imaging device hardware 260 may have any resolution. The imaging device hardware 260 may be a camera or the like. In some embodiments, one or more optical components, such as a mirror, fish-eye lens, or any other type of lens may be optically coupled to the imaging device hardware 260.

It should be understood that the components illustrated in FIG. 2 are merely illustrative and are not intended to limit the scope of this disclosure. More specifically, while the components in FIG. 2 are illustrated as residing within the data gathering device 112, this is a nonlimiting example. In some embodiments, one or more of the components may reside external to the data gathering device 112. Similarly, one or more of the components may be embodied in other devices not specifically described herein.

Figure 3:
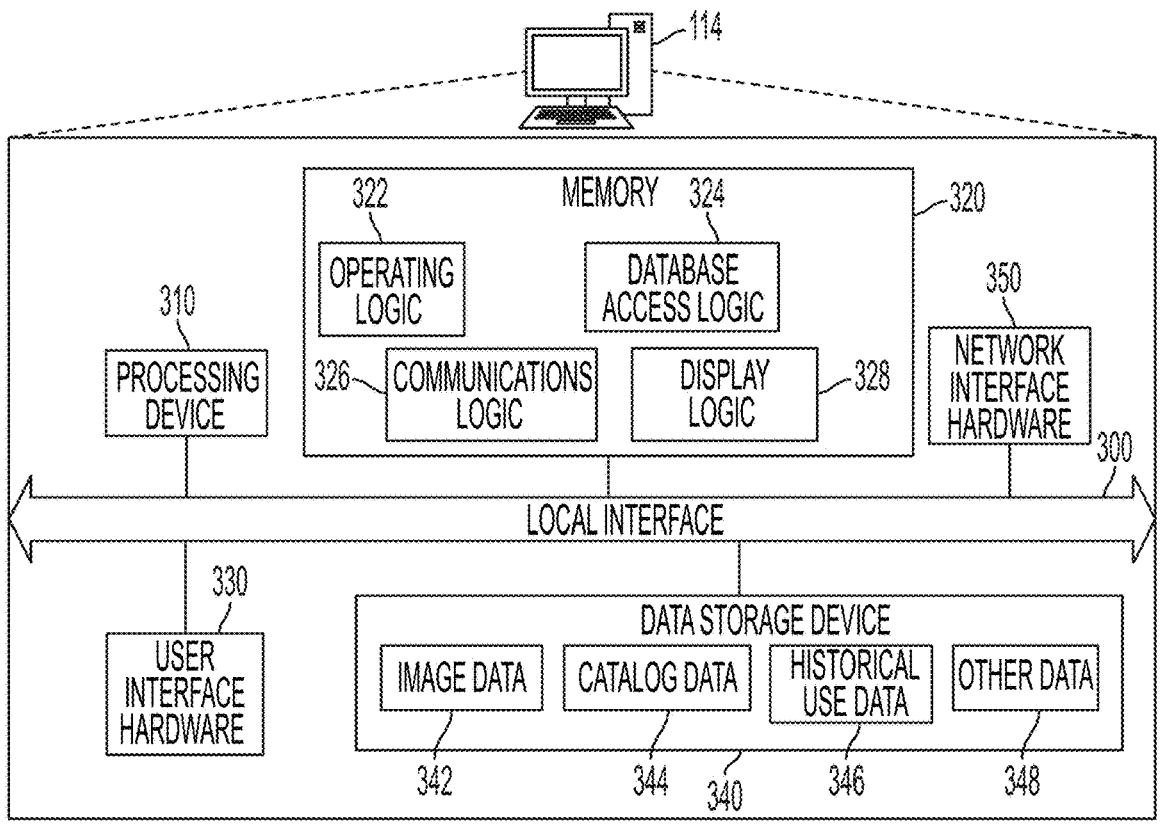
FIG. 3 schematically depicts a block diagram of illustrative internal components of a user interface device in a facility monitoring system according to one or more embodiments shown or described herein.

FIG. 3 depicts illustrative internal components contained within the user interface device 114. As depicted in FIG. 3, the user interface device 114 may further include a local interface 300 (e.g., a bus) that communicatively interconnects the various components, including, but not limited to, a processing device 310, memory 320, user interface hardware 330, network interface hardware 350, and/or a data storage device 340.

The processing device 310, such as a computer processing unit (CPU), may be the central processing unit of the user interface device 114, performing calculations and logic operations required to execute a program. The processing device 310, alone or in conjunction with one or more of the other elements disclosed in FIG. 3, is an illustrative processing device, computing device, processor, or combination thereof, as such terms are used in this disclosure.

The memory 320, such as read only memory (ROM) and random access memory (RAM), may constitute illustrative memory devices (i.e., non-transitory, processor-readable storage media). Such memory 320 may include one or more programming instructions thereon that, when executed by the processing device 310, cause the processing device 310 to complete various processes, such as the processes described herein. Optionally, the program instructions may be stored on a tangible computer-readable medium such as a digital disk, flash memory, a memory card, a USB drive, an optical disc storage medium (e.g., Blu-ray™, CD, DVD), and/or other non-transitory, processor-readable storage media.

In some embodiments, the program instructions contained on the memory 320 may be embodied as a plurality of software modules, where each module provides programming instructions for completing one or more tasks. For example, as shown in FIG. 3, the memory 320 may contain one or more of operating logic 322, database access logic 324, communications logic 326, and display logic 328. The operating logic 322 may include an operating system and/or other software for managing components of the user interface device 114 and/or providing a general user interface to a user.

The database access logic 324 may generally include programming instructions for communicating with a database server (e.g., the facility database server 116 and/or the database server 126 depicted in FIG. 1) such that data from the database server can be displayed at the user interface device 114. As such, the database access logic 324 may include programming instructions for connecting to a database server, transmitting a request for data, and receiving data from a database server.

Still referring to FIG. 3, the communications logic 326 may generally include programming instructions for transmitting and/or receiving one or more signals to/from an external object via the network interface hardware 350 (e.g., signals to/from the facility database server 116 and/or the database server 126 depicted in FIG. 1) and/or the like. For example, the communications logic 326 may contain programming instructions for operating the network interface hardware 350 such that one or more signals and/or data can be transmitted/received, as described herein.

Still referring to FIG. 3, the display logic 328 may generally include programming instructions for generating one or more user interfaces and/or components thereof that are displayed to a user via the user interface hardware 330. In some embodiments, the display logic 328 may display data retrieved via the database access logic 324 and may allow a user to manipulate the data in various manners. For example, a user may manipulate data to observe one or more trends, historical information, current information, and/or the like, as described in greater detail herein.

It should be understood that the various logic modules described herein with respect to FIG. 3 are merely illustrative, and that other logic modules, including logic modules that combine the functionality of two or more of the modules described hereinabove, may be used without departing from the scope of the present application.

Still referring to FIG. 3, the data storage device 340, which may generally be a storage medium that is separate from the memory 320, may contain a data repository for storing electronic data. The data storage device 340 may be any physical storage medium, including, but not limited to, a hard disk drive (HDD), memory, removable storage, and/or the like.

Illustrative data that may be contained within the data storage device 340 may include, for example, image data 342, catalog data 344, historical use data 346, and/or other data 348. In some embodiments, at least a portion of the data contained within the data storage device 340 may generally be data that is temporarily stored for the purposes of providing a user interface to a user.

The image data 342 generally includes images captured by the imaging device hardware 260 of the data gathering device 112 described herein with respect to FIG. 2. That is, still referring to FIG. 3, the image data 342 may include one or more images of barcodes, product packaging, and/or the like. The image data 342 may be presented via a user interface such that a user can verify a particular product associated with a particular record, update a record, and/or the like. In some embodiments, the image data 342 may be data that is temporarily obtained from an external device (e.g., the facility database server 116) and stored for the purposes of displaying on a user interface such that the user interface can provide the data more quickly than would be possible over a network connection. As such, the data may be erased from the data storage device 340 after being provided via the user interface.

The catalog data 344 may generally be data that is logged by the data gathering device 112 (FIG. 2) for the purposes of tracking personnel, procedures, products, number of units, and/or the like. The catalog data 344 may be presented via a user interface such that a user can verify a particular product associated with a particular record, update a record, view a record (or a plurality of records in the aggregate), and/or the like. In some embodiments, the catalog data 344 may be data that is temporarily obtained from an external device (e.g., the facility database server 116) and stored for the purposes of displaying on a user interface such that the user interface can provide the data more quickly than would be possible over a network connection. As such, the data may be erased from the data storage device 340 after being provided via the user interface.

The historical use data 346 may generally be data that is logged by the data gathering device 112 (FIG. 2) for the purposes of tracking personnel, procedures, products, number of units, and/or the like over a particular period of time, such as one week, one month, a plurality of months (e.g., a quarter), a year, a plurality of years, and/or the like. The historical use data 346 may be presented via a user interface such that a user can view trends pertaining to use of a particular product, trends pertaining to a particular procedure, trends pertaining to particular personnel, pricing history, and/or the like. In some embodiments, the historical use data 346 may be data that is temporarily obtained from an external device (e.g., the facility database server 116) and stored for the purposes of displaying on a user interface such that the user interface can provide the data more quickly than would be possible over a network connection. As such, the data may be erased from the data storage device 340 after being provided via the user interface.

The other data 348 is not limited by the present disclosure, and may generally be any other data that is generated and/or stored as a result of operation of the user interface device 114 or component thereof.

The user interface hardware 330 may generally include hardware that is used to provide an interface between a user and the various components of the user interface device 114. For example, the user interface hardware 330 may include one or more buttons and/or toggles and/or a display. The user interface hardware 330 may permit information from the local interface 300 to be displayed on the display in audio, visual, graphic, or alphanumeric format in some embodiments. For example, the display may be configured to display a broadcasting status. The buttons and/or toggles may allow for transmission of inputs from a user. In some embodiments, particularly embodiments where the user interface device 114 is a device having a touchscreen display, the display and the buttons and/or toggles may be integrated into a single component.

The network interface hardware 350 may generally provide the user interface device 114 with an ability to interface with one or more components external to the user interface device 114. For example, the network interface hardware 350 may be used to facilitate communication between the user interface device 114 and one or more of the other components communicatively coupled to the network 100 depicted in FIG. 1. Still referring to FIG. 3, communication with external devices may occur using various communication ports (not shown). An illustrative communication port may be attached to a communications network, such as the Internet, an intranet, a local network, a direct connection, and/or the like. In some embodiments, the network interface hardware 350 may include any wired or wireless networking hardware, such as a modem, LAN port, wireless fidelity (Wi-Fi) card, WiMax card, Long Term Evolution (LTE) hardware, mobile communications hardware, and/or other hardware for communicating with other networks and/or devices.

It should be understood that the components illustrated in FIG. 3 are merely illustrative and are not intended to limit the scope of this disclosure. More specifically, while the components in FIG. 3 are illustrated as residing within the user interface device 114, this is a nonlimiting example. In some embodiments, one or more of the components may reside external to the user interface device 114. Similarly, one or more of the components may be embodied in other devices not specifically described herein.

Figure 4:
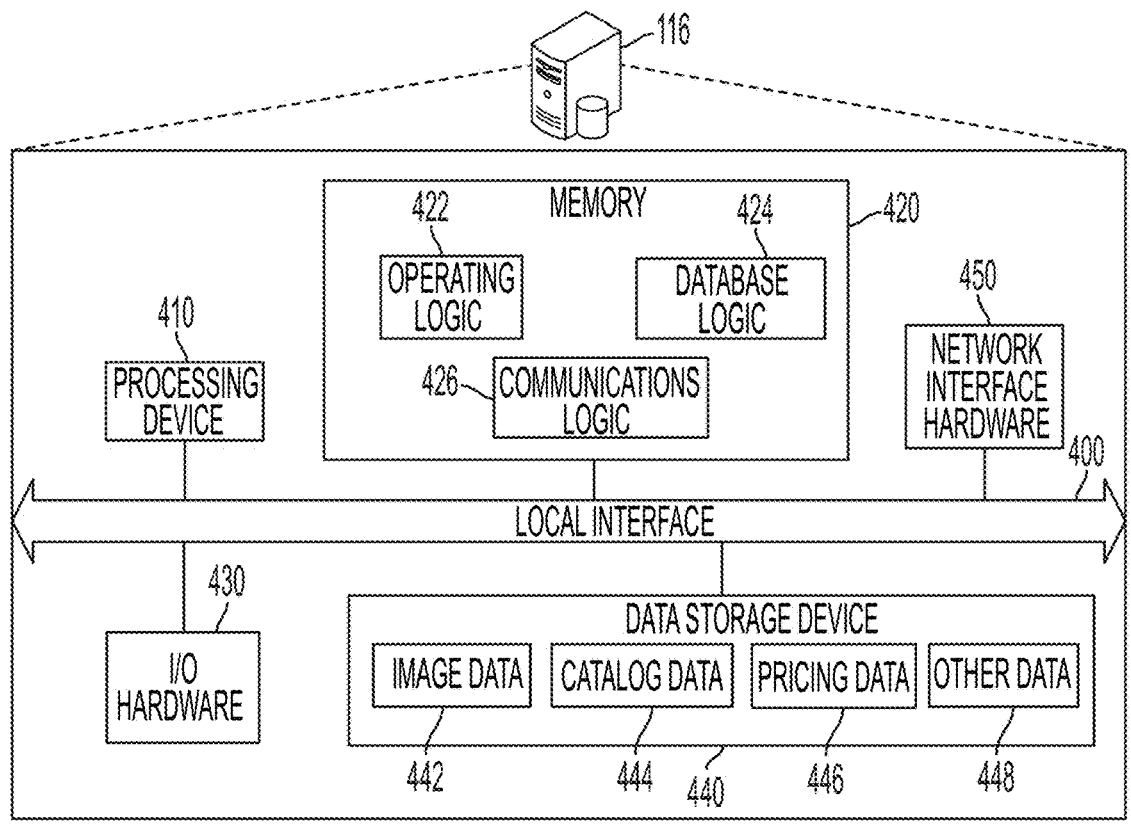
FIG. 4 schematically depicts a block diagram of illustrative internal components of a facility database server in a facility monitoring system according to one or more embodiments shown or described herein.

As illustrated in FIG. 4, the facility database server 116 may include a processing device 410, a non-transitory memory component 420, input/output (I/O) hardware 430, network interface hardware 450, and/or a data storage device 440. A local interface 400, such as a bus or the like, may interconnect the various components.

The processing device 410, such as a computer processing unit (CPU), may be the central processing unit of the facility database server 116, performing calculations and logic operations to execute a program. The processing device 410, alone or in conjunction with the other components, is an illustrative processing device, computing device, processor, or combination thereof. The processing device 410 may include any processing component configured to receive and execute instructions (such as from the data storage device 440 and/or the memory component 420).

The memory component 420 may be configured as a volatile and/or a nonvolatile computer-readable medium and, as such, may include random access memory (including SRAM, DRAM, and/or other types of random access memory), read only memory (ROM), flash memory, registers, compact discs (CD), digital versatile discs (DVD), and/or other types of storage components. The memory component 420 may include one or more programming instructions thereon that, when executed by the processing device 410, cause the processing device 410 to complete various processes, such as the various processes described herein.

The programming instructions stored on the memory component 420 may be embodied as a plurality of software logic modules, where each logic module provides programming instructions for completing one or more tasks. Illustrative logic modules depicted in FIG. 4 include, but are not limited to, operating logic 422, database logic 424, and/or communications logic 426.

Each of the logic modules shown in FIG. 4 may be embodied as a computer program, firmware, or hardware, as an example. The operating logic 422 may include an operating system and/or other software for managing components of the facility database server 116. The database logic 424 may generally include programming instructions for accessing a database, including instructions for writing a record to a database, erasing a record from a database, and modifying a record in a database. The communications logic 426 may generally include programming instructions for transmitting and/or receiving one or more signals and/or data to/from an external object via the network interface hardware 450 and/or the I/O hardware 430 (e.g., signals to/from the various components connected to the network 100 of FIG. 1) and/or the like.

Still referring to FIG. 4, the I/O hardware 430 may communicate information between the local interface 400 and one or more external components that may be used during operation of the facility database server 116. For example, the I/O hardware 430 may act as an interface between an external data storage device and other components of the facility database server 116, so as to facilitate data transfer between the external data storage device and the facility database server 116.

The network interface hardware 450 may include any wired or wireless networking hardware, such as a modem, LAN port, wireless fidelity (Wi-Fi) card, WiMax card, mobile communications hardware, and/or other hardware for communicating with other networks and/or devices. For example, the network interface hardware 450 may be used to facilitate communication between the facility database server 116 and the various other components connected to the network 100 (FIG. 1). Still referring to FIG. 4, in some embodiments, the I/O hardware 430 and the network interface hardware 450 may be integrated into a single device that handles all communications to and from the facility database server 116.

The data storage device 440, which may generally be a storage medium, may contain one or more data repositories for storing data that is received and/or generated. The data storage device 440 may be any physical storage medium, including, but not limited to, a hard disk drive (HDD), memory, removable storage, and/or the like. While the data storage device 440 is depicted as a local device, it should be understood that the data storage device 440 may be a remote storage device, such as, for example, a server computing device, cloud based storage device, or the like. Illustrative data that may be contained within the data storage device 440 includes, but is not limited to, image data 442, catalog data 444, pricing data 446, and/or other data 448.

The image data 442 generally includes images captured by the imaging device hardware 260 of the data gathering device 112 described herein with respect to FIG. 2. That is, still referring to FIG. 4, the image data 442 may include one or more images of barcodes, product packaging, and/or the like. The image data 442 is stored such that it can be provided to one or more other components coupled to the network 100 (FIG. 1) upon request. For example, referring to FIGS. 1 and 4, the image data 442 may contain one or more images that, when requested by the user interface device 114 and/or the data gathering device 112, are copied and transmitted by the facility database server 116 (e.g., via the network interface hardware 450 and/or the I/O hardware 430) to the user interface device 114 and/or the data gathering device.

Referring to FIGS. 2 and 4, the catalog data 444 may generally be data that is logged by the data gathering device 112 for the purposes of tracking personnel, procedures, products, number of units, and/or the like. The catalog data 444 is stored as a record of a facility's use of particular products, a number of units of each particular product for each procedure, a number and type(s) of procedure performed, an identity (e.g., name, position, etc.) of personnel performing each procedure, and/or the like. In some embodiments, the catalog data 444 may be data that is collected and transmitted to an external component, such as, for example, one or more components of the product provider system 120 (FIG. 1). In some embodiments, the catalog data 444 may be verified for accuracy before being transmitted to an external component. (e.g., reviewed via a user interface on the user interface device 114 (FIG. 3).

The pricing data 446 may generally be data that pertains to pricing of a particular product, as described herein. Referring to FIGS. 1 and 4, the information received that is stored as part of the pricing data 446 may be received from one or more components of the product provider system 120, such as, for example, the determination device 122 of the product provider system 120. The pricing data 446 is generally not modifiable by the various components of the facility monitoring system 110, but rather just accessible to components of the facility monitoring system 110. For example, a user of the data gathering device 112 and/or the user interface device 114 may access the pricing data 446 to view pricing for a particular product, pricing history, average pricing, and/or the like.

Referring again to FIG. 4, the other data 448 is not limited by the present disclosure, and may generally be any other data that is generated and/or stored as a result of operation of the facility database server 116 or component thereof.

It should be understood that the components illustrated in FIG. 4 are merely illustrative and are not intended to limit the scope of this disclosure. More specifically, while the components in FIG. 4 are illustrated as residing within the facility database server 116, this is a nonlimiting example. In some embodiments, one or more of the components may reside external to the facility database server 116. In addition, the facility database server 116 may also include other components not specifically described herein, such as, for example, one or more user interface devices.

Figure 5:
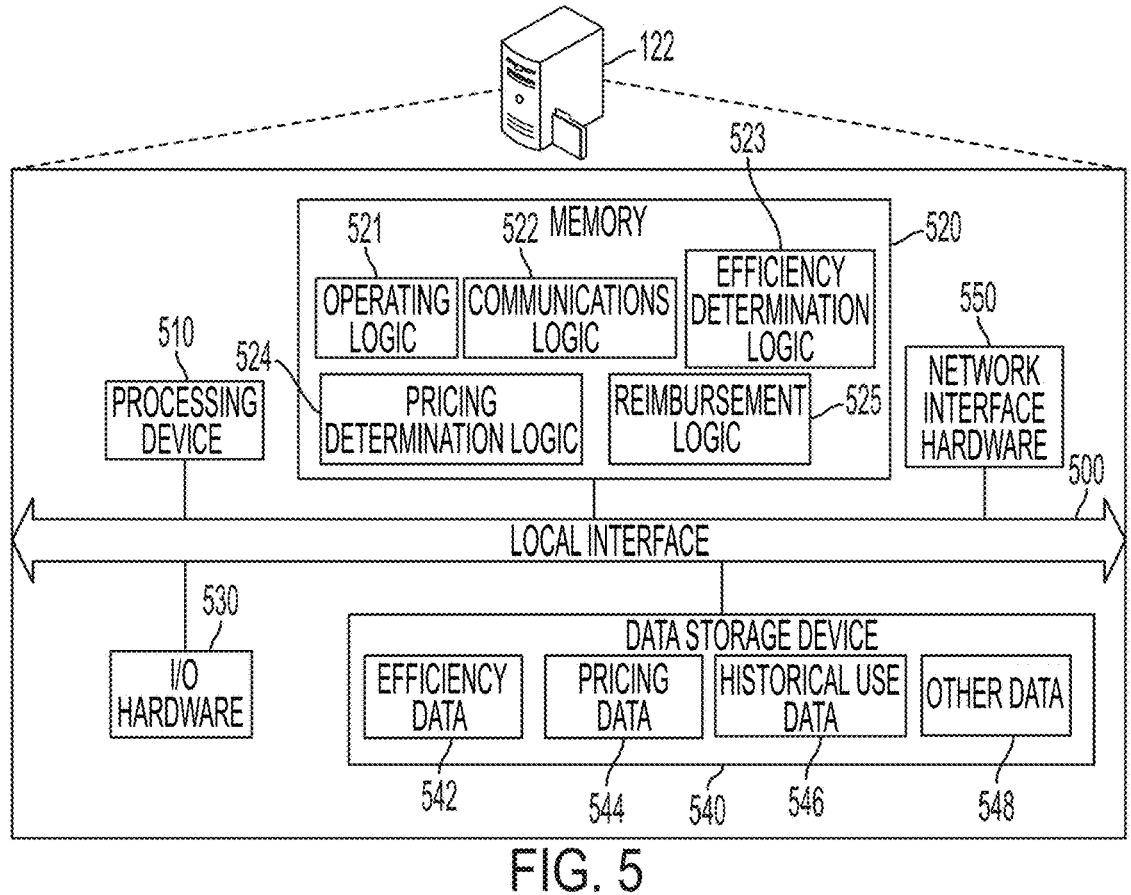
FIG. 5 schematically depicts a block diagram of illustrative internal components of a rebate and efficiency determination device in a product provider system according to one or more embodiments shown or described herein.

As described herein, the determination device 122 is generally a device that receives the collected data from one or more of the components of the facility monitoring system 110, performs analytics on the data, executes one or more machine learning processes with the data, generates a machine learning model using the data, determines information pertaining to an average or expected number of units of a particular product per procedure, determines information pertaining to an expected efficiency of use of a particular product for a particular procedure, determines pricing based on determined information, and/or the like. As illustrated in FIG. 5, the determination device 122 may include a processing device 510, a non-transitory memory component 520, input/output (110) hardware 530, network interface hardware 550, and/or a data storage device 540. A local interface 500, such as a bus or the like, may interconnect the various components.

The processing device 510, such as a computer processing unit (CPU), may be the central processing unit of the determination device 122, performing calculations and logic operations to execute a program. The processing device 510, alone or in conjunction with the other components, is an illustrative processing device, computing device, processor, or combination thereof. The processing device 510 may include any processing component configured to receive and execute instructions (such as from the data storage device 540 and/or the memory component 520).

The memory component 520 may be configured as a volatile and/or a nonvolatile computer-readable medium and, as such, may include random access memory (including SRAM, DRAM, and/or other types of random access memory), read only memory (ROM), flash memory, registers, compact discs (CD), digital versatile discs (DVD), and/or other types of storage components. The memory component 520 may include one or more programming instructions thereon that, when executed by the processing device 510, cause the processing device 510 to complete various processes, such as the various processes described herein.

The programming instructions stored on the memory component 520 may be embodied as a plurality of software logic modules, where each logic module provides programming instructions for completing one or more tasks. Illustrative logic modules depicted in FIG. 5 include, but are not limited to, operating logic 521, communications logic 522, efficiency determination logic 523, pricing determination logic 524, and/or reimbursement logic 525.

Each of the logic modules shown in FIG. 5 may be embodied as a computer program, firmware, or hardware, as an example. The operating logic 521 may include an operating system and/or other software for managing components of the determination device 122.

The communications logic 522 may generally include programming instructions for transmitting and/or receiving one or more signals and/or data to/from an external object via the network interface hardware 550 and/or the I/O hardware 530 (e.g., signals to/from the various components connected to the network 100 of FIG. 1) and/or the like.

Still referring to FIG. 5, the efficiency determination logic 523 includes programming instructions for determining an efficiency of use of a particular product for a particular procedure. That is, the efficiency determination logic 523 contains programming instructions for determining how many units of a particular product anticipated to be used for a particular procedure, determining how many units is considered to be efficient based on the determined number of units that anticipated to be used, and determining how many units is considered to be inefficient based on the determined number of units that anticipated to be used. For example, if a determination is made that five units of a particular product are anticipated to be used for a particular procedure, a determination that anything equal to or less than five units (e.g., 1 unit to 5 units) may be considered efficient and anything greater than five units (e.g., 6 or more units) may be considered inefficient.

In some embodiments, the efficiency determination logic 523 may be a machine learning module that generates and continuously updates a trained model that is based on historical use. The trained model may be used for the purposes of determining how many units of a particular product are considered to be an efficient use of the particular product for a particular procedure. In some embodiments, the trained model may be trained to determine an efficient use based on particular variables, such as the personnel performing a procedure, the subject on which the procedure is being performed, and/or the like. As additional data is fed into the trained model, the trained model is able to more accurately predict a number of units to be used for the purposes of determining efficiency. In some embodiments, the efficiency determination logic 523 may be separate from the determination device 122 (e.g., as a separate machine learning server or the like) that is communicatively coupled to the determination device 122 to provide information pertaining to a determined efficiency of a particular product use.

The pricing determination logic 524 includes programming instructions for determining price to be offered for a particular product based on the efficiency of use of the particular product. That is, the pricing determination logic 524 contains programming instructions for determining a price per procedure that will result in particular pricing goals for the seller of the product being met based on the number of procedures that are being completed for a particular period of time. In some embodiments, the pricing determination logic 524 may contain programming for determining tiers of pricing based on a closeness of a particular facility's use of a product to the expected efficiency. For example, if an expected efficiency is five units per procedure, a facility may be given a first tier of pricing (e.g., a best pricing tier at a rate that represents the lowest price per procedure) if the facility averages five units per procedure. The facility may be given a second tier of pricing (e.g., a better pricing tier that is not as good as the best pricing tier and represents a higher price per procedure than the best pricing tier) if the facility is averaging 6-8 units per procedure. The facility may be given a third tier of pricing (e.g., a standard pricing tier that is not as good as the better pricing tier and represents an even higher price per procedure than the better pricing tier) if the facility is averaging 8 units per procedure or more. It should be understood that the tiers provided herein are merely illustrative and other pricing tiers are also contemplated without departing from the scope of the present disclosure.

In some embodiments, the pricing determination logic 524 may be a machine learning module that generates and continuously updates a trained model that is based on historical use and/or pricing. The trained model may be used for the purposes of determining what a price per procedure should be, as well as any pricing tiers, as described above. In some embodiments, the trained model may be trained to determine a pricing based on particular variables, such as the personnel performing a procedure, the subject on which the procedure is being performed, and/or the like. As additional data is fed into the trained model, the trained model is able to more accurately predict a pricing to be used. In some embodiments, the pricing determination logic 524 may be separate from the determination device 122 (e.g., as a separate machine learning server or the like) that is communicatively coupled to the determination device 122 to provide information pertaining to a determined pricing.

The reimbursement logic 525 includes programming instructions for determining a reimbursement amount and generating a reimbursement check, wire transfer, and/or the like. For example, the reimbursement logic 525 may determine, for a particular period of time (e.g., a previous month, a previous quarter, or the like), how much was paid up front for a given number of units of a product that were used. The reimbursement logic 525 may further determine a number of procedures completed in the same particular period of time and calculate an amount owed, which represents the number of procedures times the price per procedure to be charged, as determined by the pricing determination logic 524. The reimbursement logic 525 then determines the amount to be reimbursed, which represents the amount paid up front minus the amount owed. A check, wire transfer, ACH transfer, and/or the like is then issued for the amount owed to the facility (or manager of the facility) that paid for the product up front.

Still referring to FIG. 5, the I/O hardware 530 may communicate information between the local interface 500 and one or more external components that may be used during operation of the determination device 122. For example, the I/O hardware 530 may act as an interface between an external data storage device and other components of the determination device 122, so as to facilitate data transfer between the external data storage device and the determination device 122.

The network interface hardware 550 may include any wired or wireless networking hardware, such as a modem, LAN port, wireless fidelity (Wi-Fi) card, WiMax card, mobile communications hardware, and/or other hardware for communicating with other networks and/or devices. For example, the network interface hardware 550 may be used to facilitate communication between the determination device 122 and the various other components connected to the network 100 (FIG. 1). Still referring to FIG. 5, in some embodiments, the I/O hardware 530 and the network interface hardware 550 may be integrated into a single device that handles all communications to and from the determination device 122.

The data storage device 540, which may generally be a storage medium, may contain one or more data repositories for storing data that is received and/or generated. The data storage device 540 may be any physical storage medium, including, but not limited to, a hard disk drive (HDD), memory, removable storage, and/or the like. While the data storage device 540 is depicted as a local device, it should be understood that the data storage device 540 may be a remote storage device, such as, for example, a server computing device, cloud based storage device, or the like. Illustrative data that may be contained within the data storage device 540 includes, but is not limited to, efficiency data 542, pricing data 544, historical use data 546, and/or other data 548.

The efficiency data 542 generally includes data pertaining to an efficiency of use of a particular product by particular personnel for a particular procedure as determined by the efficiency determination logic 523. In some embodiments, the efficiency data 542 may also include data pertaining to an expected efficiency, which may be based on a particular product, particular personnel using the product, a particular procedure, a particular subject upon which the procedure is performed, and/or the like.

The pricing data 544 may generally be data that pertains to pricing of a particular product, as described herein. The pricing data 544 may be generated as a result of operation according to the program instructions contained in the pricing determination logic 524. As such, the pricing data 544 may include data pertaining to a determined price per procedure of a particular product for a particular procedure. Further, the pricing data 544 may include data pertaining to one or more determined tiers of pricing, as described herein.

The historical use data 546 generally includes data pertaining to actual use of a particular product by particular personnel for a particular procedure. The historical use data 546 may include historical use for a particular period of time, such as, for example, a week, a plurality of weeks, a month, a plurality of months (e.g., a quarter (3 months), two quarters (six months), or the like), a year, a plurality of years, or the like.

The other data 548 is not limited by the present disclosure, and may generally be any other data that is generated and/or stored as a result of operation of the determination device 122 or component thereof.

It should be understood that the components illustrated in FIG. 5 are merely illustrative and are not intended to limit the scope of this disclosure. More specifically, while the components in FIG. 5 are illustrated as residing within the determination device 122, this is a nonlimiting example. In some embodiments, one or more of the components may reside external to the determination device 122. In addition, the determination device 122 may also include other components not specifically described herein, such as, for example, one or more user interface devices.

Figure 6:
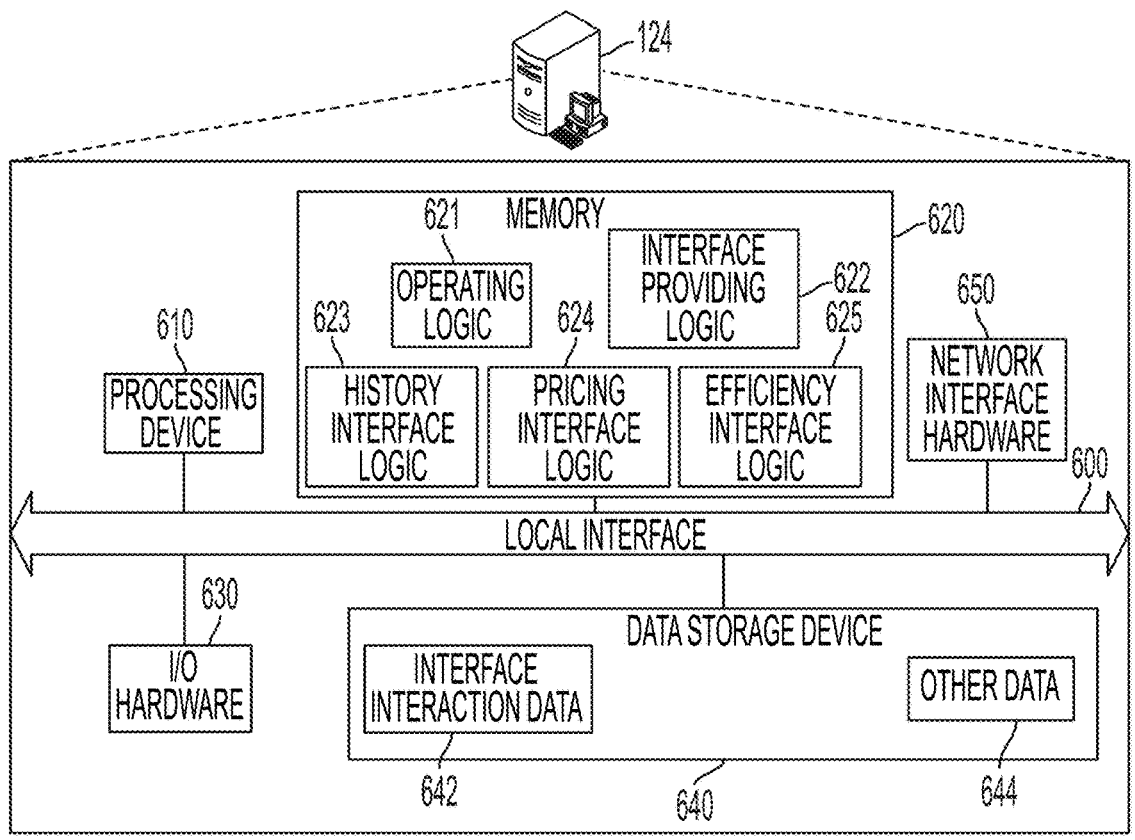
FIG. 6 schematically depicts a block diagram of illustrative internal components of a interface provider in a product provider system according to one or more embodiments shown or described herein.

As illustrated in FIG. 6, the interface provider 124 may include a processing device 610, a non-transitory memory component 620, input/output (110) hardware 630, network interface hardware 650, and/or a data storage device 640. A local interface 600, such as a bus or the like, may interconnect the various components.

The processing device 610, such as a computer processing unit (CPU), may be the central processing unit of the interface provider 124, performing calculations and logic operations to execute a program. The processing device 610, alone or in conjunction with the other components, is an illustrative processing device, computing device, processor, or combination thereof. The processing device 610 may include any processing component configured to receive and execute instructions (such as from the data storage device 640 and/or the memory component 620).

The memory component 620 may be configured as a volatile and/or a nonvolatile computer-readable medium and, as such, may include random access memory (including SRAM, DRAM, and/or other types of random access memory), read only memory (ROM), flash memory, registers, compact discs (CD), digital versatile discs (DVD), and/or other types of storage components. The memory component 620 may include one or more programming instructions thereon that, when executed by the processing device 610, cause the processing device 610 to complete various processes, such as the various processes described herein.

The programming instructions stored on the memory component 620 may be embodied as a plurality of software logic modules, where each logic module provides programming instructions for completing one or more tasks. Illustrative logic modules depicted in FIG. 6 include, but are not limited to, operating logic 621, interface providing logic 622, history interface logic 623, pricing interface logic 624, and/or efficiency interface logic 625.

Each of the logic modules shown in FIG. 6 may be embodied as a computer program, firmware, or hardware, as an example. The operating logic 622 may include an operating system and/or other software for managing components of the interface provider 124. The interface providing logic 622 may generally include instructions for providing a user interface to a user for the purposes of displaying generated information, receiving user inputs, and/or the like. Referring to FIGS. 1 and 6, the interface providing logic 622 may generally provide the interface on a device that is external to the interface provider 124, such as an interface on the one or more data gathering devices 112 and/or the user interface device 114. That is, the user interfaces provided on the one or more data gathering devices 112 and/or the user interface device 114 may be at least partially provided by the software programming contained within the interface providing logic 622. Other parts of the user interface may be provided by the history interface logic 623, the pricing interface logic 624, and/or the efficiency interface logic 625. That is, the history interface logic 623 may provide an interface specific to a use history to a user, the pricing interface logic 624 may provide an interface specific to determined pricing to a user, and the efficiency interface logic 625 may provide an interface specific to determined efficiency to a user, as described herein.

Referring again to FIG. 6, the I/O hardware 630 may communicate information between the local interface 600 and one or more external components that may be used during operation of the interface provider 124. For example, the I/O hardware 630 may act as an interface between an external data storage device and other components of the interface provider 124, so as to facilitate data transfer between the external data storage device and the interface provider 124.

The network interface hardware 650 may include any wired or wireless networking hardware, such as a modem, LAN port, wireless fidelity (Wi-Fi) card, WiMax card, mobile communications hardware, and/or other hardware for communicating with other networks and/or devices. For example, the network interface hardware 650 may be used to facilitate communication between the interface provider 124 and the various other components connected to the network 100 (FIG. 1). Still referring to FIG. 6, in some embodiments, the I/O hardware 630 and the network interface hardware 650 may be integrated into a single device that handles all communications to and from the interface provider 124.

The data storage device 640, which may generally be a storage medium, may contain one or more data repositories for storing data that is received and/or generated. The data storage device 640 may be any physical storage medium, including, but not limited to, a hard disk drive (HDD), memory, removable storage, and/or the like. While the data storage device 640 is depicted as a local device, it should be understood that the data storage device 640 may be a remote storage device, such as, for example, a server computing device, cloud based storage device, or the like. Illustrative data that may be contained within the data storage device 640 includes, but is not limited to, interface interaction data 642 and/or other data 644. The interface interaction data 642 may generally contain data pertaining to an interaction between a user and the user interface provided by the programming contained in the memory component 620. For example, the interface interaction data 642 may include a log of one or more button clicks, scrolling, and/or the like. The interface interaction data 642 may also include information pertaining to how data is viewed, sorted, and/or the like. The other data 644 is not limited by the present disclosure, and may generally be any other data that is generated and/or stored as a result of operation of the interface provider 124 or component thereof.

It should be understood that the components illustrated in FIG. 6 are merely illustrative and are not intended to limit the scope of this disclosure. More specifically, while the components in FIG. 6 are illustrated as residing within the interface provider 124, this is a nonlimiting example. In some embodiments, one or more of the components may reside external to the interface provider 124. In addition, the interface provider 124 may also include other components not specifically described herein, such as, for example, one or more user interface devices.

Figure 7:
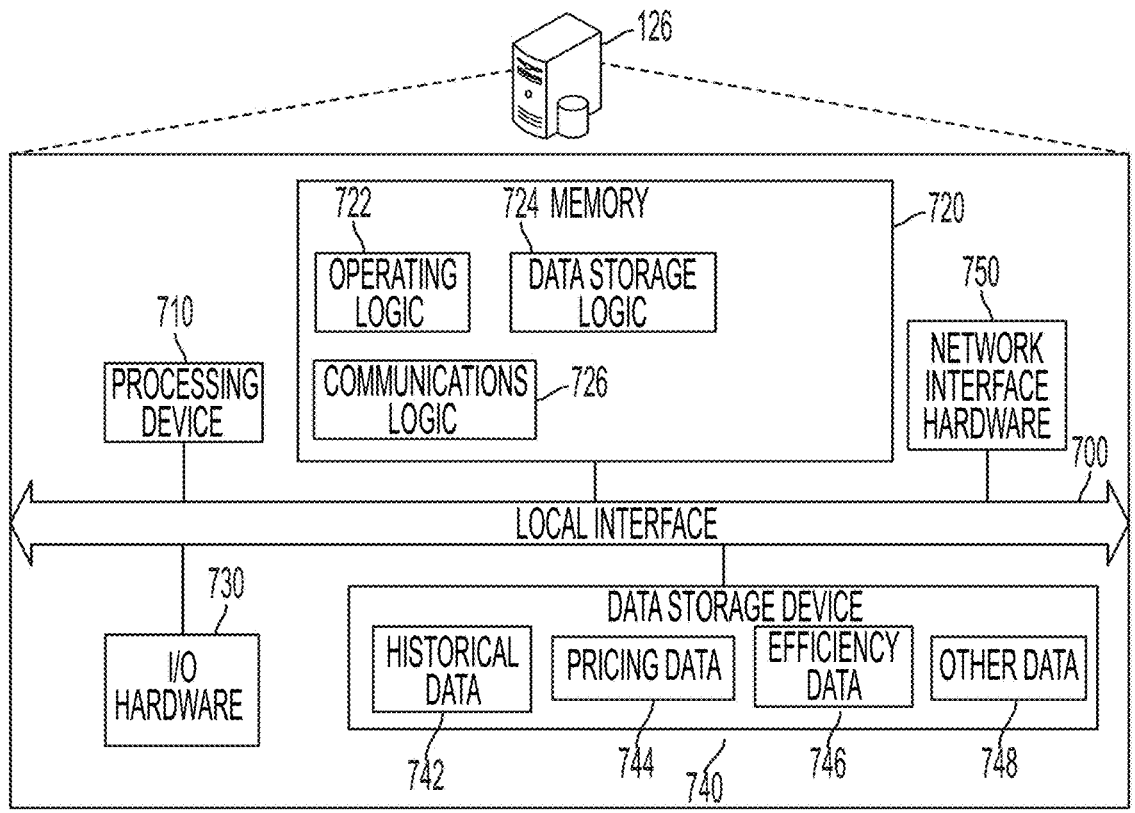
FIG. 7 schematically depicts a block diagram of illustrative internal components of a rebate and efficiency database server in a product provider system according to one or more embodiments shown or described herein.

As illustrated in FIG. 7, the database server 126 may include a processing device 710, a non-transitory memory component 720, input/output (110) hardware 730, network interface hardware 750, and/or a data storage device 740. A local interface 700, such as a bus or the like, may interconnect the various components.

The processing device 710, such as a computer processing unit (CPU), may be the central processing unit of the database server 126, performing calculations and logic operations to execute a program. The processing device 710, alone or in conjunction with the other components, is an illustrative processing device, computing device, processor, or combination thereof. The processing device 710 may include any processing component configured to receive and execute instructions (such as from the data storage device 740 and/or the memory component 720).

The memory component 720 may be configured as a volatile and/or a nonvolatile computer-readable medium and, as such, may include random access memory (including SRAM, DRAM, and/or other types of random access memory), read only memory (ROM), flash memory, registers, compact discs (CD), digital versatile discs (DVD), and/or other types of storage components. The memory component 720 may include one or more programming instructions thereon that, when executed by the processing device 710, cause the processing device 710 to complete various processes, such as the various processes described herein.

The programming instructions stored on the memory component 720 may be embodied as a plurality of software logic modules, where each logic module provides programming instructions for completing one or more tasks. Illustrative logic modules depicted in FIG. 7 include, but are not limited to, operating logic 722, data storage logic 724, and/or communications logic 726.

Each of the logic modules shown in FIG. 7 may be embodied as a computer program, firmware, or hardware, as an example. The operating logic 722 may include an operating system and/or other software for managing components of the database server 126. The data storage logic 724 may generally include programming instructions for accessing a database, including instructions for writing a record to a database, erasing a record from a database, and modifying a record in a database. The communications logic 726 may generally include programming instructions for transmitting and/or receiving one or more signals and/or data to/from an external object via the network interface hardware 750 and/or the I/O hardware 730 (e.g., signals to/from the various components connected to the network 100 of FIG. 1) and/or the like.

Still referring to FIG. 7, the I/O hardware 730 may communicate information between the local interface 700 and one or more external components that may be used during operation of the database server 126. For example, the I/O hardware 730 may act as an interface between an external data storage device and other components of the database server 126, so as to facilitate data transfer between the external data storage device and the database server 126.

The network interface hardware 750 may include any wired or wireless networking hardware, such as a modem, LAN port, wireless fidelity (Wi-Fi) card, WiMax card, mobile communications hardware, and/or other hardware for communicating with other networks and/or devices. For example, the network interface hardware 750 may be used to facilitate communication between the database server 126 and the various other components connected to the network 100 (FIG. 1). Still referring to FIG. 7, in some embodiments, the I/O hardware 730 and the network interface hardware 750 may be integrated into a single device that handles all communications to and from the database server 126.

The data storage device 740, which may generally be a storage medium, may contain one or more data repositories for storing data that is received and/or generated. The data storage device 740 may be any physical storage medium, including, but not limited to, a hard disk drive (HDD), memory, removable storage, and/or the like. While the data storage device 740 is depicted as a local device, it should be understood that the data storage device 740 may be a remote storage device, such as, for example, a server computing device, cloud based storage device, or the like. Illustrative data that may be contained within the data storage device 740 includes, but is not limited to, historical data 742, pricing data 744, efficiency data 746, and/or other data 748.

The historical data 742 generally includes data pertaining to actual use of a particular product by particular personnel for a particular procedure. The historical data 742 may include historical use for a particular period of time, such as, for example, a week, a plurality of weeks, a month, a plurality of months (e.g., a quarter (3 months), two quarters (six months), or the like), a year, a plurality of years, or the like.

The pricing data 744 may generally be data that pertains to pricing of a particular product, as described herein. The pricing data 744 may be generated as a result of operation according to the program instructions contained in the pricing determination logic 524 of the determination device 122 (FIG. 5). As such, the pricing data 744 may include data pertaining to a determined price per procedure of a particular product for a particular procedure. Further, the pricing data 744 may include data pertaining to one or more determined tiers of pricing, as described herein.

Still referring to FIG. 7, the efficiency data 746 generally includes data pertaining to an efficiency of use of a particular product by particular personnel for a particular procedure as determined by the efficiency determination logic 523 of the determination device 122 (FIG. 5). Still referring to FIG. 7, in some embodiments, the efficiency data 746 may also include data pertaining to an expected efficiency, which may be based on a particular product, particular personnel using the product, a particular procedure, a particular subject upon which the procedure is performed, and/or the like.

The other data 748 is not limited by the present disclosure, and may generally be any other data that is generated and/or stored as a result of operation of the database server 126 or component thereof.

It should be understood that the components illustrated in FIG. 7 are merely illustrative and are not intended to limit the scope of this disclosure. More specifically, while the components in FIG. 7 are illustrated as residing within the database server 126, this is a nonlimiting example. In some embodiments, one or more of the components may reside external to the database server 126. In addition, the database server 126 may also include other components not specifically described herein, such as, for example, one or more user interface devices.

It should now be understood that the various components described herein with respect to FIGS. 1-7 function to obtain information regarding one or more products used during procedures, as well as a number of units of each product used. Additional data that can be used for the purposes of more accurately predicting expected use is also obtained. The various components described herein with respect to FIGS. 1-7 can then determine, based on the obtained information, what constitutes efficient use and determine pricing to assign to a particular product at a per-procedure rate. The various components described herein with respect to FIGS. 1-7 can also calculate a rebate owed based on the determined pricing and the pricing paid per unit up front.

As mentioned above, the various components described with respect to FIGS. 1-7 may be used to carry out one or more processes and/or provide functionality for obtaining use information pertaining to one or more products, one or more procedures, one or more personnel, and/or the like, determining a pricing of a particular product based on the use information, issuing rebates for products based on a determined price and an up-front price paid, establishing a pricing tier, and/or the like. An illustrative example of the various processes are described with respect to FIGS. 8, 19, 27, and 28 hereinbelow.

Figure 8:
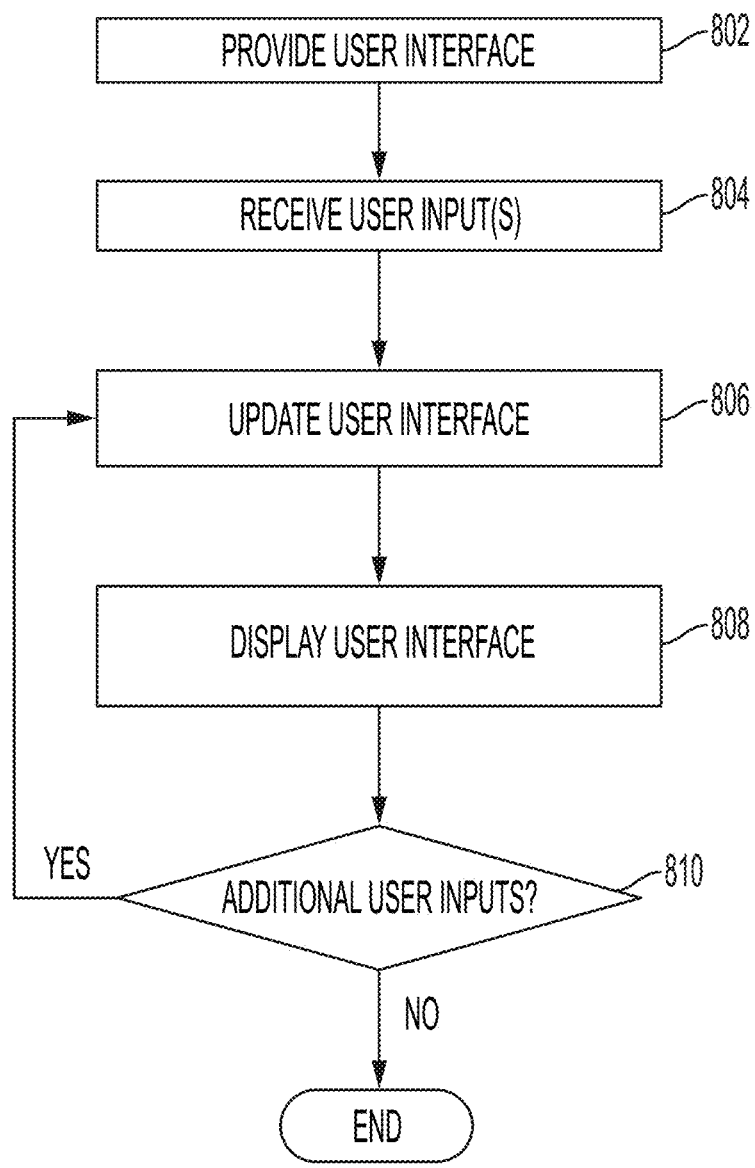
FIG. 8 depicts a flow diagram of an illustrative overview method of obtaining information from a user for the purposes of determining efficiency and pricing according to one or more embodiments shown or described herein.

FIG. 8 depicts an illustrative overview process of providing a user interface and receiving one or more user inputs that pertain to entry of a product used for a particular procedure, as described herein. At block 802, a user interface is provided. At block 804, one or more user inputs are received. At block 806, the user interface is updated in response to the user inputs, and the user interface, with the updates, is displayed at block 808. The process may repeat at block 806 if a decision is made at block 810 that additional inputs are received. The process may end if no additional inputs are received. FIGS. 9-19 depict an illustrative user interface 900 that may be updated according to the processes depicted in FIG. 8.

Figure 9:
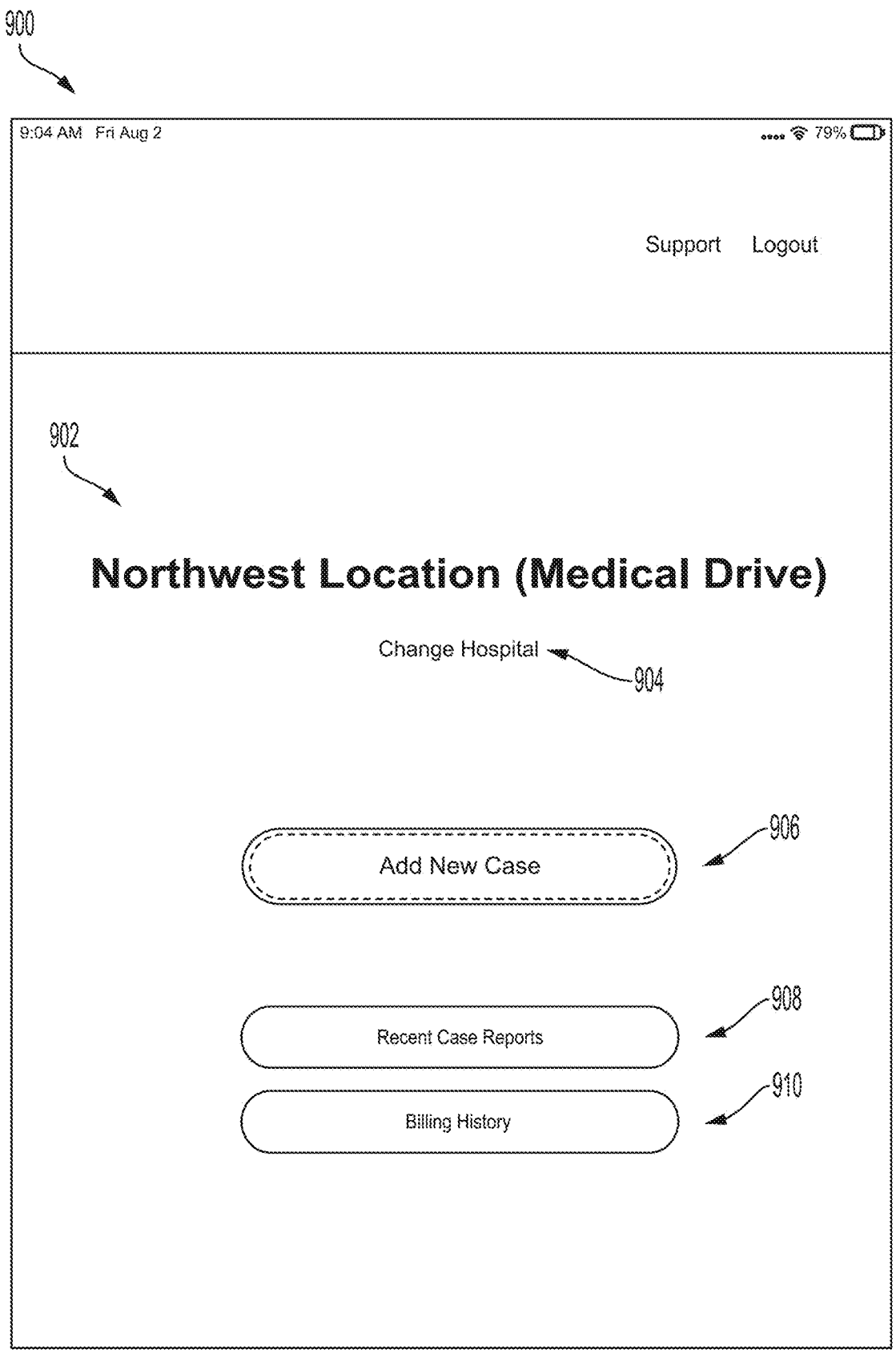
FIG. 9 schematically depicts a screen shot of an illustrative user interface according to one or more embodiments shown or described herein.

FIG. 9 depicts the user interface 900 that may be provided in an initial state. As depicted in FIG. 9. The user interface 900 may have a facility name field 902, a selectable option 904 to change the facility, and/or an "add new case" selection button 906. In the embodiment depicted in FIG. 9, the user interface 900 may have additional fields such as a "recent case reports" selection button 908 and/or a "billing history" selection button 910.

Figure 10:
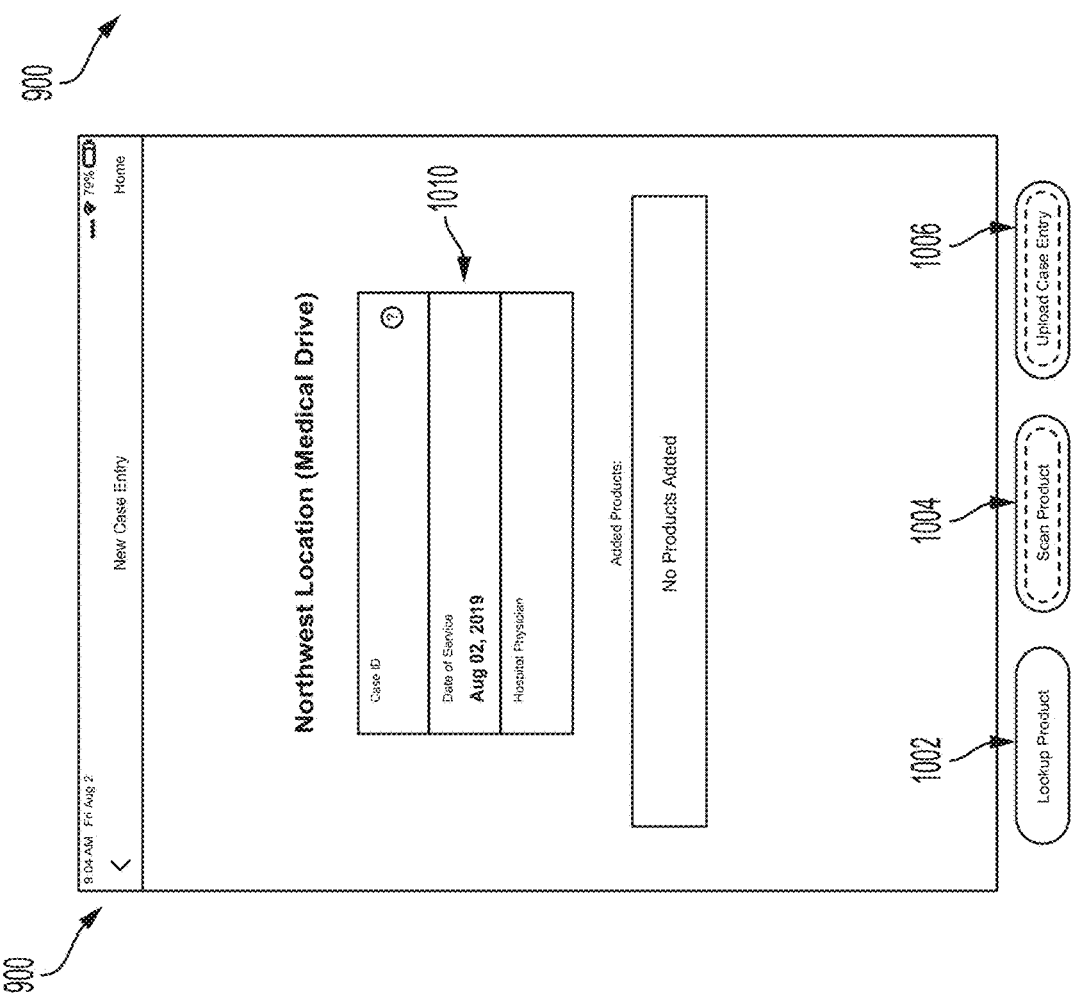
FIG. 10 schematically depicts a screen shot of an illustrative user interface having a data entry screen according to one or more embodiments shown or described herein.

If a user selects the "add new case" selection button 906 in the user interface 900, the user interface 900 may provide one or more selectable buttons for adding a new case and products used, as shown in FIG. 10. More specifically, the user interface 900 may be updated to display a "lookup product" selection button 1002, a "scan product" selection button 1004, and "upload case entry" selection button 1006. Also depicted in FIG. 10 is a plurality of detail fields 1010 where a user can enter specifics regarding a particular procedure, such as, for example, a Case ID number, a date of service, the name of the physician or other medical personnel performing the procedure, certain non-identifying details regarding the subject on which the procedure is being performed (e.g., height, weight, particular diseases, etc.), and/or the like.

Figure 11:
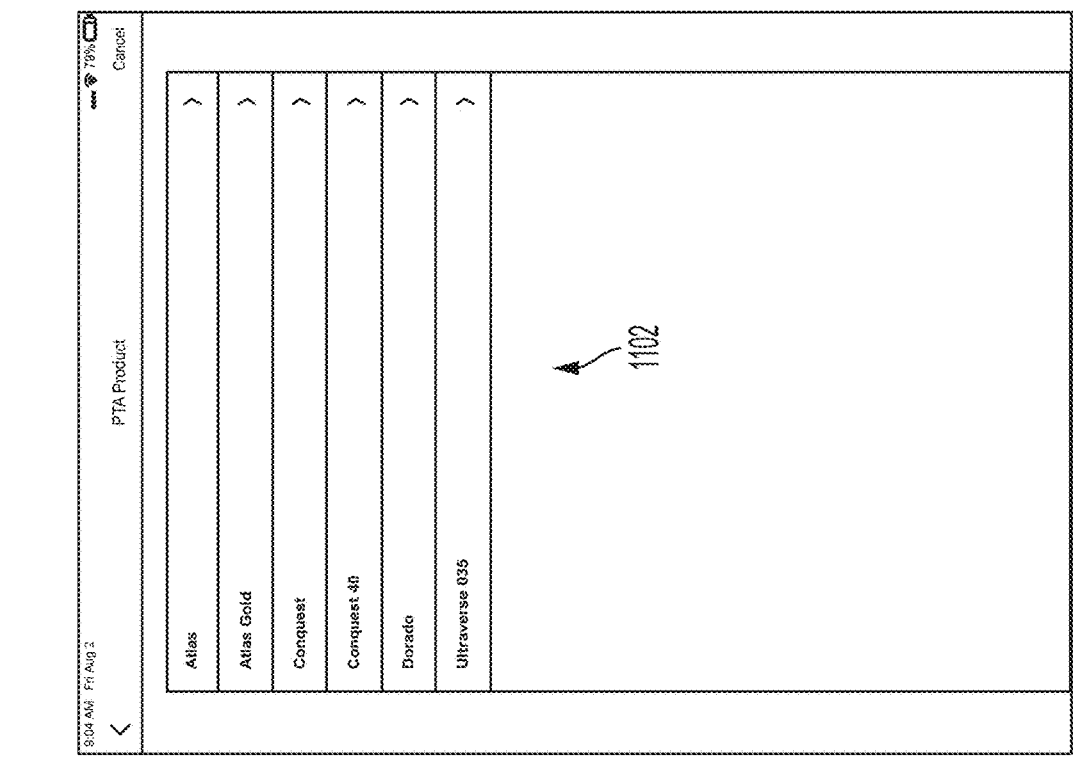
FIG. 11 schematically depicts a screen shot of an illustrative user interface having a product selection screen according to one or more embodiments shown or described herein.
Figures 12, 13:
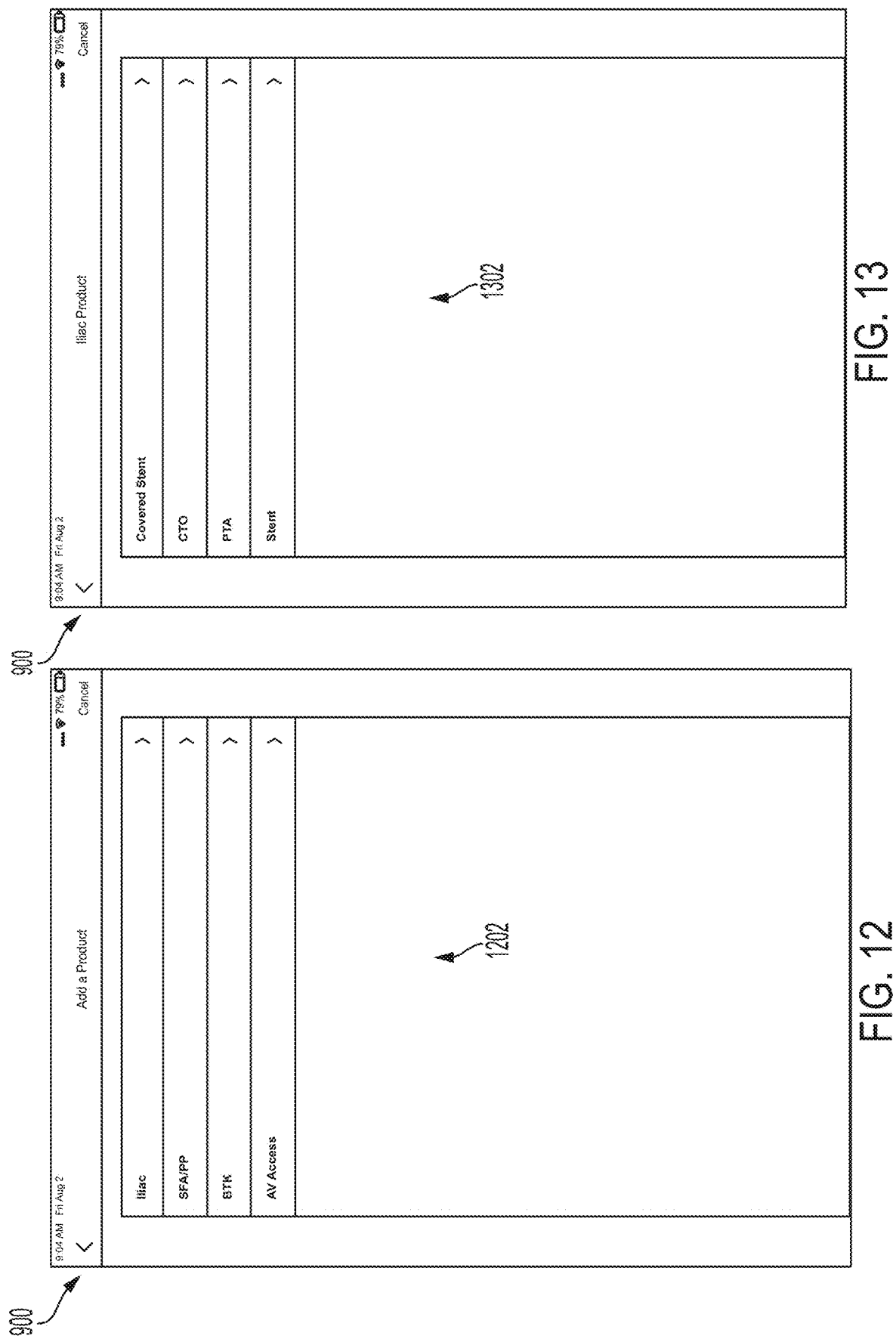
FIG. 12 schematically depicts a screen shot of an illustrative user interface having a procedure selection screen according to one or more embodiments shown or described herein.
FIG. 13 schematically depicts a screen shot of an illustrative user interface having an iliac product selection screen according to one or more embodiments shown or described herein.

If a user selects the "lookup product" selection button 1002, the user interface 900 may be updated as shown in FIG. 11 to display a pick list 1102 of products that may have been used during a procedure, such as products identified by their associated trademarks as "atlas," "atlas gold," "conquest," "conquest 40," "dorado," and "ultraverse 035" for example. Upon selecting an option, the user interface 900 may be updated as shown in FIG. 12 to depict illustrative procedures to be selected in a procedure pick list 1202. For example, in the embodiment depicted in FIG. 12, the procedures the user may select from include are iliac procedures, a superficial femoral artery (SFA) procedure, a below the knee (BTK) procedure, an arteriovenous (AV) procedure, and/or the like. Other procedures are also contemplated, including, but not limited to, a biopsy procedure, a surgical procedure, a vascular treatment procedure (e.g., treatment of critical limb ischemia (CLI)), a transjugular intrahepatic portosystemic shunt (TIPS) procedure, and/or the like.

Once a user selects a procedure, a more particular device pick list 1302 may be shown in the user interface 900 as updated and shown in FIG. 13. As depicted in the embodiment of FIG. 13, illustrative examples of particular devices from which a user can pick in the device pick list 1302 include, but are not limited to, covered stents, chronic total occlusion (CTO) related products, percutaneous transluminal angioplasty (PTA) related products, uncovered stents, or the like.

Figures 14, 15A:
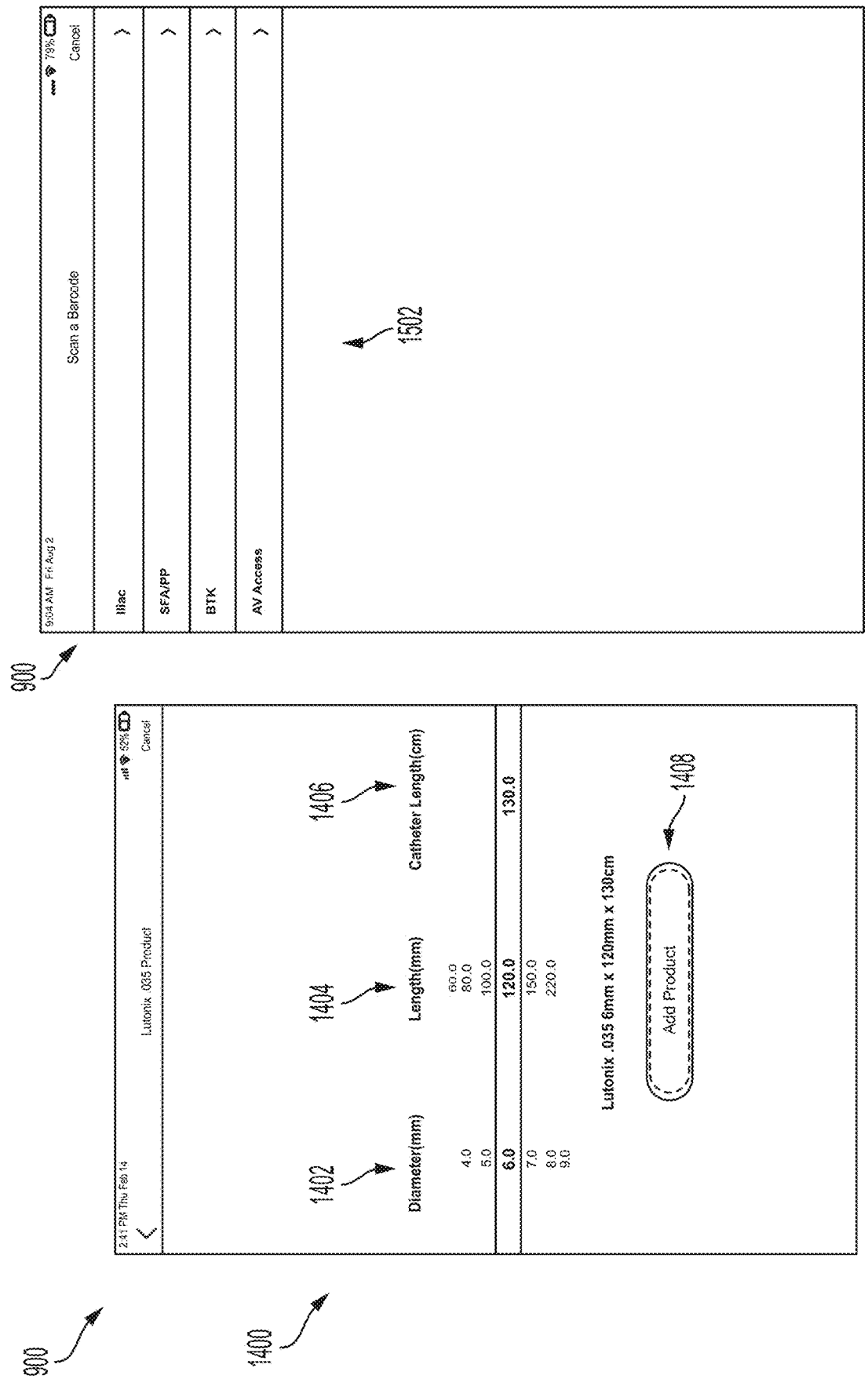
FIG. 14 schematically depicts a screen shot of an illustrative user interface having a product picker according to one or more embodiments shown or described herein.
FIG. 15A schematically depicts a screen shot of an illustrative user interface having a body area selector according to one or more embodiments shown or described herein.

Once a user selects a product, a product details pick list 1400 may be shown in the user interface 900 as updated and shown in FIG. 14. The product details pick list may include a plurality of options, such as, for example, a product diameter 1402, a product length 1404, and/or a catheter length 1406. Once the appropriate options have been selected by the user, the user may select an "add product" button 1408 to add the product to a record being generated.

Figures 15B, 16:
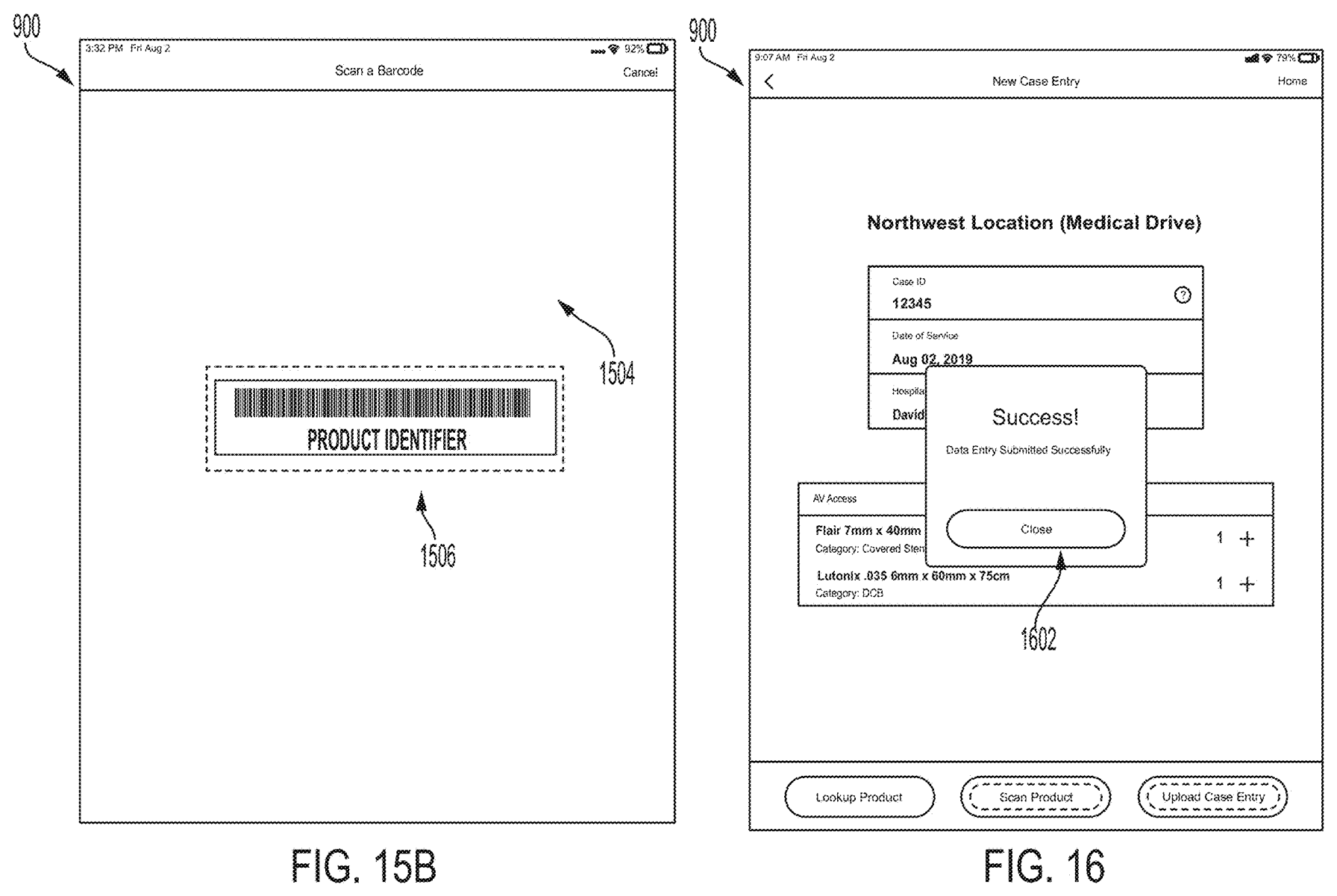

Referring again to FIG. 10, if a user selects the "scan product" selection button 1004, the user interface may be updated as shown in FIG. 15A for a user to select a type of procedure or body area being performed prior to scanning a barcode in a procedure/body area pick list 1502. For example, in the embodiment depicted in FIG. 15A, the procedures/body areas the user may select from include are iliac procedures, a superficial femoral artery (SFA) procedure, a below the knee (BTK) procedure, an arteriovenous (AV) procedure, and/or the like. Once the procedure/body area has been selected, a barcode interface 1504 is provided, as shown in FIG. 15B. The user can place the barcode for the product in view of the imaging device hardware 260 (FIG. 2) such that a box 1506 bounds the barcode in the barcode interface 1504.

Referring to FIG. 16, once information has been entered via the user interface 900, the user may receive a notification 1602 or the like that indicates whether the information has been successfully entered. For example, the embodiment of FIG. 16 depicts a pop up screen indicating that the entry of information was successful.

Figure 17:
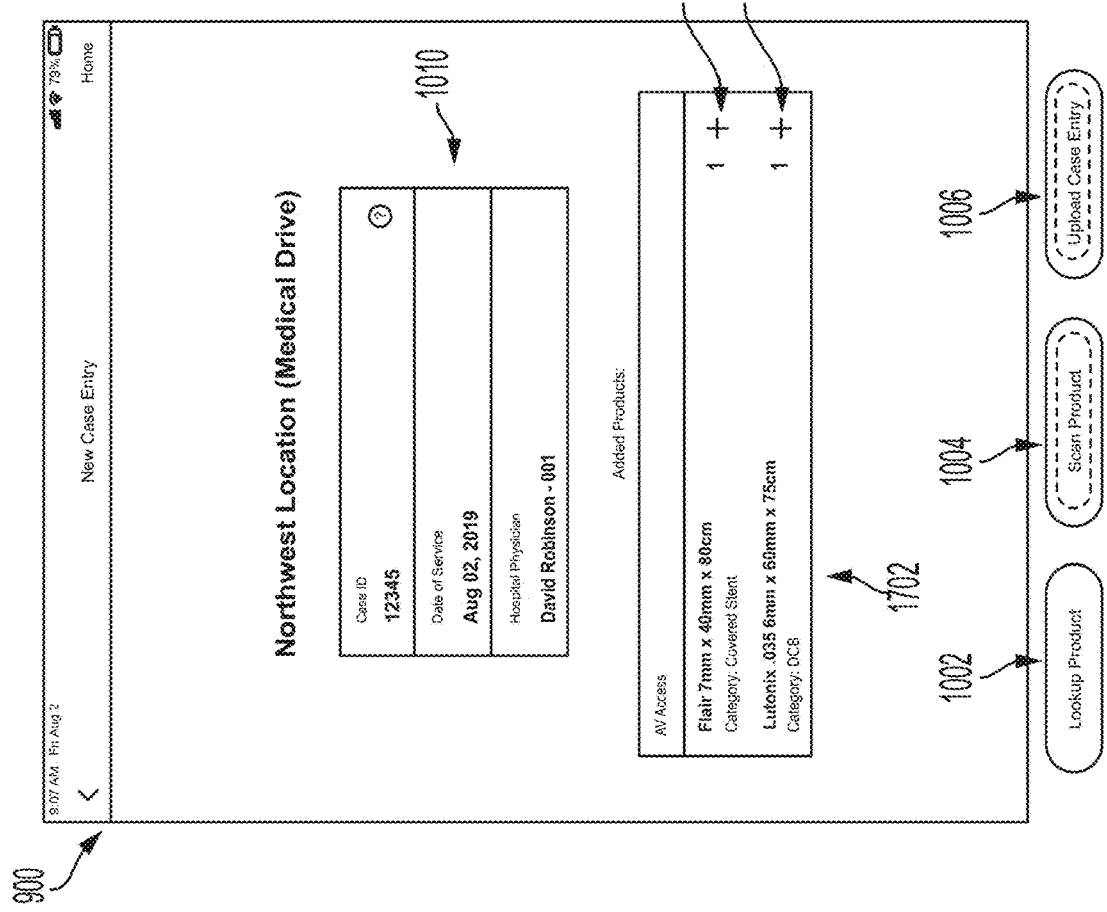
FIG. 17 schematically depicts a screen shot of an illustrative user interface including a modifiable list of products added to a procedure according to one or more embodiments shown or described herein.

The user interface 900 may be updated as shown in FIG. 17 to indicate which products have been used for a particular procedure, as shown in a product display window 1702. The user may further click the "lookup product" selection button 1002, the "scan product" selection button 1004, or the "upload case entry" selection button 1006 to further update the record. In addition, the user may indicate a number of units of a product that was used by clicking the "+" indicator 1704 next to the associated product in the product display window in some embodiments.

Figure 18:
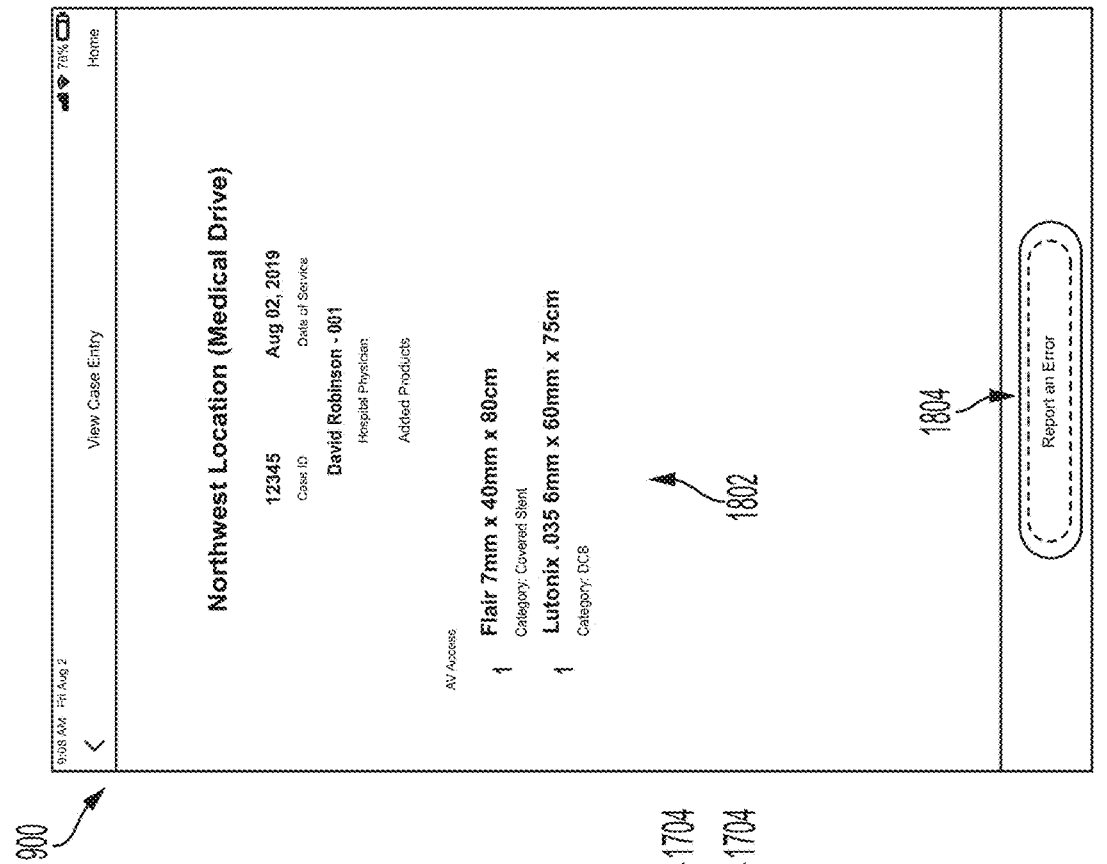
FIG. 18 schematically depicts a screen shot of an illustrative user interface including a finalized record of products included in a procedure according to one or more embodiments shown or described herein.

In some embodiments, an entry may be automatically be closed or selected by the user to be closed such that the user interface depicts a finalized record 1802 depicted in FIG. 18. The finalized record 1802 is then sent to one or more components such as, for example, the facility database server 116 and/or the database server 126 of FIG. 1. If a user desires to modify the finalized record 1802, the user may press a "report an error" button 1804, which returns the user to the user interface 900 depicted in FIG. 17 for further modification.

Figure 19:
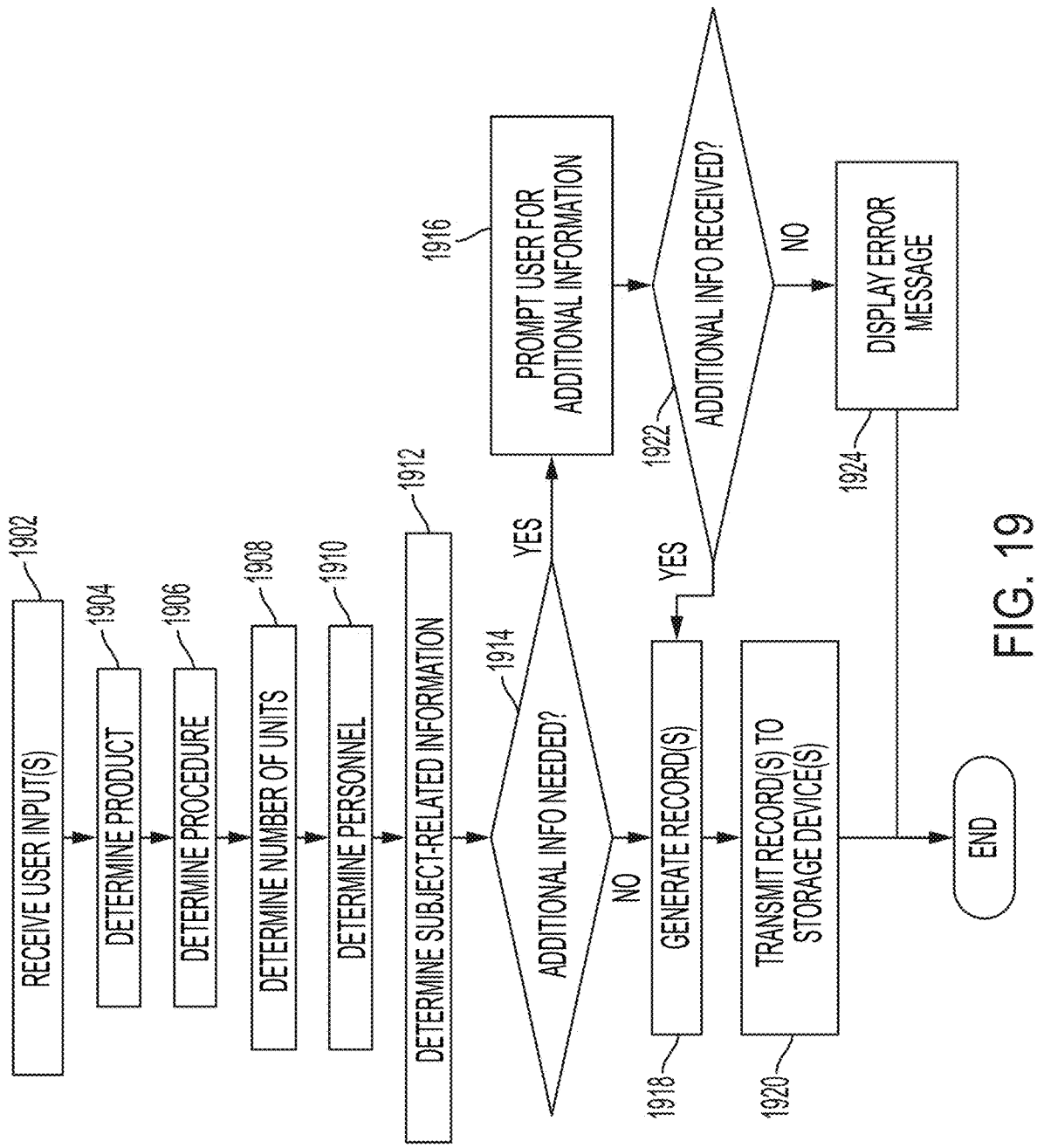
FIG. 19 schematically depicts a flow diagram of an illustrative method of receiving one or more user inputs and generating records according to one or more embodiments shown or described herein.

Additional details regarding receipt of a user entry of data pertaining to a product is depicted in FIG. 19. More specifically, FIG. 19 depicts a flow diagram of an illustrative method of receiving one or more data entries from a user via a user interface (e.g., a user interface on the one or more data gathering devices 112 depicted in FIG. 1). Still referring to FIG. 19, one or more user inputs are received at block 1902. That is, the one or more user inputs are received via the user interface. At block 1904, the product is determined from the one or more user inputs. For example, the product is determined based on the product that was selected by the user, as described herein. In another example, the product is determined based on the product packaging that was imaged by the user, as described herein. At block 1906, the procedure is determined from the one or more user inputs. For example, the procedure is determined based on the selected procedure selected by the user, as described herein. At block 1908, the number of units is determined. For example, the number of units is determined based on the number of units indicated by the user via the user interface, as described herein. At block 1910, the personnel performing the procedure and/or involved with the procedure are determined. For example, the personnel involved may be obtained from the associated fields containing personnel related data as entered by the user. At block 1912, the subject-related information is determined. For example, non-identifying information pertaining to the subject upon which the procedure was performed may be determined based on inputs received from the user.

At block 1914, a determination is made as to whether additional information is needed to complete the record. For example, if the user failed to enter data in a field, if the data in a particular field cannot be validated, and/or the like, a determination may be made that additional information is needed to complete the record. If additional information is needed, the process may proceed to block 1916. If additional information is not needed, the process may proceed to block 1918.

At block 1916, the user may be prompted to provide additional information. That is, the user interface 900 (FIGS. 8-18) may be updated to display an indicator to the user to provide more information. A determination is then made at block 1922 as to whether the user provided the additional requested information. If not, the process may proceed to block 1924 whereby an error message is displayed and the process ends without adding the record to the database. If so, the process may proceed to block 1918.

At block 1918, one or more records are generated from the information received. The one or more records contain information that can be later used for the purposes of determining an efficiency, a pricing level, and/or the like, as described herein. In some embodiments, the one or more records may be in a format that is readable by a machine learning server for the purposes of developing a model that is used to predict an expected efficiency and/or cost, as described herein. The one or more records, once generated, may be transmitted to one or more storage devices at block 1920. For example, the one or more records may be transmitted to the facility database server 116 and/or the database server 126 of FIG. 1. Once transferred, the data can be used for the purposes of determining efficiency and/or a price, as described herein. In addition, users of one or more devices, such as, for example, the one or more data gathering devices 112 (FIG. 1) and/or the user interface device 114 (FIG. 1)

may further access the data in one or more reports, as depicted in FIGS. 20-26 below.

Figures 20, 21:
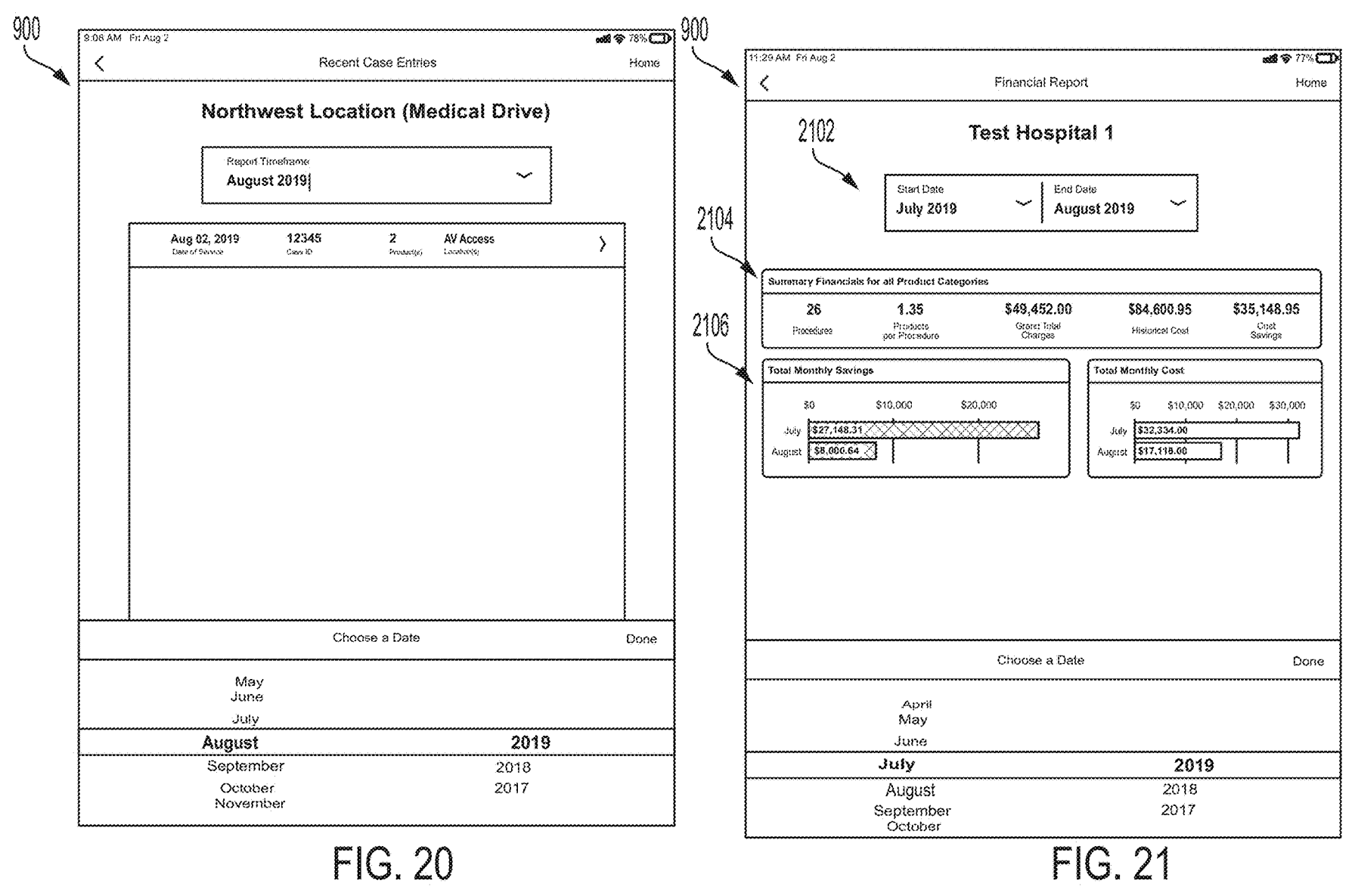

Referring to FIGS. 1 and 20, a user of a device that displays the user interface 900 (e.g., the one or more data gathering devices 112 and/or the user interface device 114) may utilize the device to display one or more reports. For example, the embodiment of FIG. 20 provides a structured means of selecting a particular report to display based on a date of which a procedure has occurred. In other embodiments, reports may be provided over a period of time. For example, FIG. 21 depicts the user interface 900 when a date range is selected in a date range field 2102. A summary field 2104 displays the number of procedures within the date range, the number of products per procedure, the total charges, the historical cost (e.g., the price per unit that is paid up front), and the cost savings. The summary field 2104 may also display other information not specifically depicted in FIG. 21. Also shown in the embodiment of FIG. 21 is a graphical view field 2106. The graphical view field 2106 graphically depicts information that may also be shown in the summary field, such as, for example, a total monthly savings for a particular product in a particular time period and/or a total monthly cost for a particular product in a particular time period.

Referring to FIG. 22, the user interface 900 may be updated to show a plurality of product entries 2202. For example, each one of the plurality of product entries 2202 may include a date of service, a case ID number, the number of products used (e.g., a number of units of a particular product), and/or a type of procedure (e.g., a location where the product is used). Other information may also be displayed without departing from the scope of the present disclosure. The user interface 900 can be adapted such that a user can sort by a particular timeframe, as indicated by a timeframe query box 2204 in FIG. 22.

Figure 23:
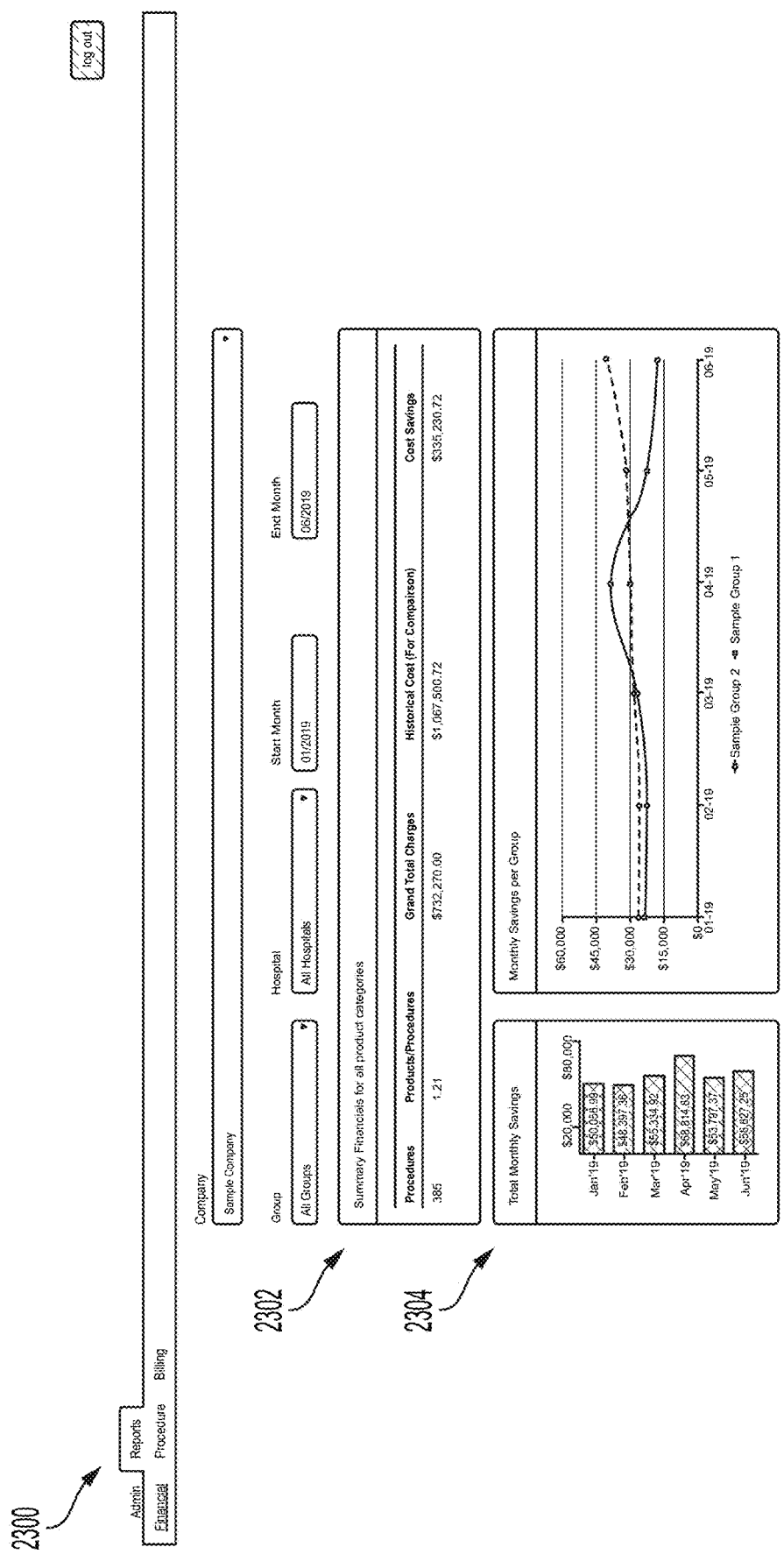
FIG. 23 schematically depicts a screen shot of an illustrative web based interface for viewing a summary of information according to one or more embodiments shown or described herein.

In some embodiments, such as the embodiment depicted in FIG. 23, a user may be able to view information in a web-based interface 2300 pertaining to how much was saved using the systems and methods described herein. For example, FIG. 23 depicts a summary financials field 2302 that includes information such as, but not limited to, a number of procedures, an average number of products per procedure, a grand total charge, a historical cost (e.g., an upfront cost paid), and a cost savings. The summary financials field 2302 may also display other information not specifically depicted in in FIG. 23. Also shown in the embodiment of FIG. 23 is a graphical view field 2304. The graphical view field 2304 graphically depicts information that may also be shown in the summary field, such as, for example, a total monthly savings for a particular product in a particular time period and/or a total monthly cost for a particular product in a particular time period. In some embodiments, the web-based interface 2300 depicted in FIG. 23 may be similar to the user interface 900 depicted in FIG. 21.

Figure 25:
FIG. 25 schematically depicts a screen shot of an illustrative web based interface for viewing yet another summary of information according to one or more embodiments shown or described herein.
Figure 27:
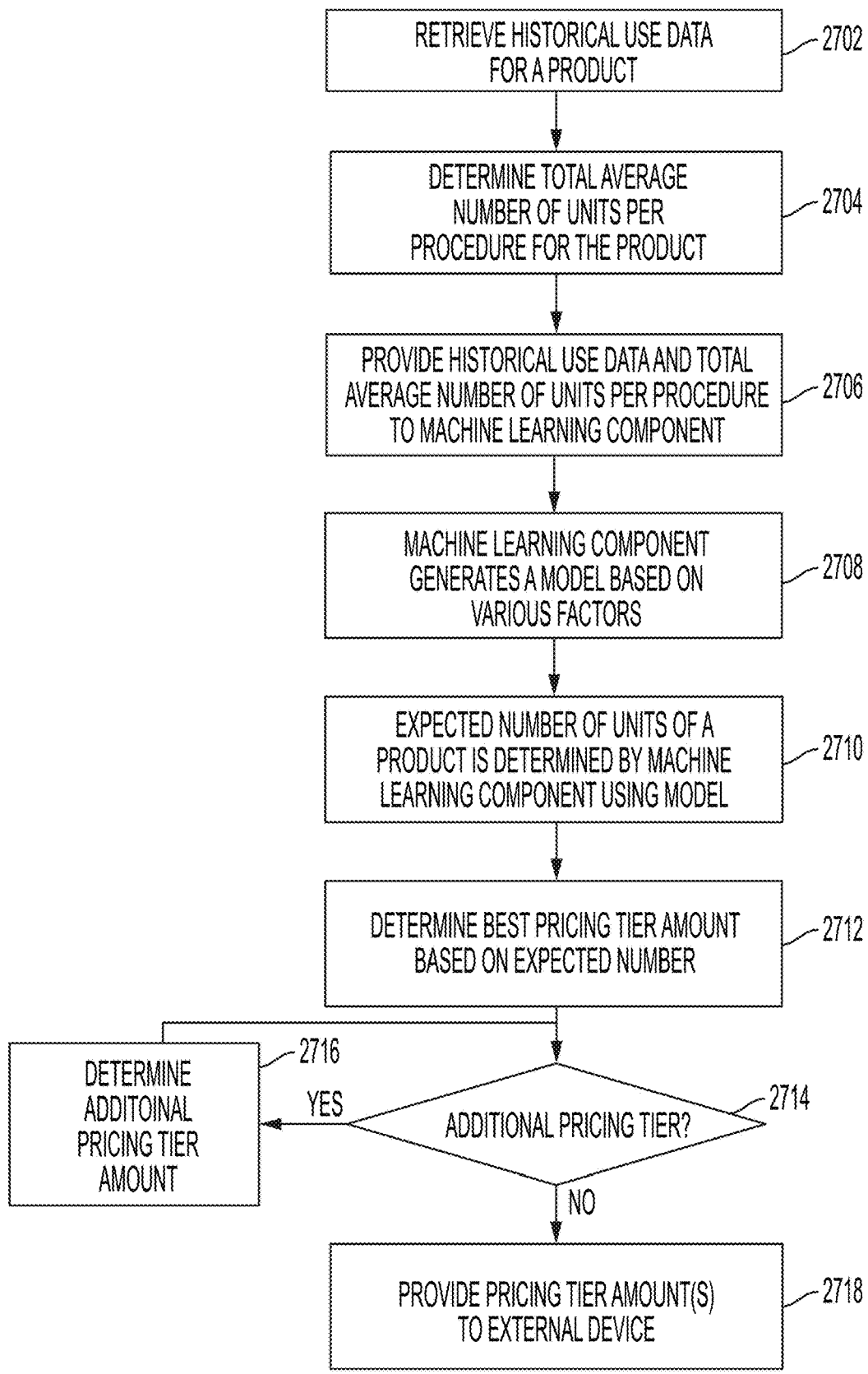
FIG. 27 schematically depicts a flow diagram of an illustrative method of determining an expected number of units and a pricing according to one or more embodiments shown or described herein.

FIG. 24 depicts other information that may be displayed by the web-based interface 2300. More specifically, FIG. 24 depicts a chart that includes information such as, but not limited to, a case ID number, an account name (e.g., a facility name), a date of service, the last time information was uploaded, the name of any personnel (e.g., physicians), a product category, a product family, a detailed description of the product, and the number of units used. FIG. 25 depicts still other information that may also be displayed by the web-based interface 2300, including, but not limited to, an account name, an account number, a shipping account name, a shipping account number, billing and/or shipping addresses, billing codes, prices, number of units, and/or the like. FIG. 26 depicts additional information that may also be displayed by the web-based interface 2300. More specifically, the information depicted in FIG. 26 pertains to a determined pricing for a particular tier of pricing based on the efficiency of use of a particular product by a particular facility. For example, for billing code 100 (which may pertain to a particular product for a particular facility), the first (e.g., best) tier of pricing may be $10 per procedure. The next best pricing may be $20 per procedure, and so on. FIG. 27 described hereinbelow depicts a flow diagram of an illustrative method of determining an efficiency and the pricing displayed in FIG. 26.

Referring to FIGS. 5, 7, and 27, at block 2702, historical use data is retrieved by the determination device 122. In some embodiments, the historical use data 546 is retrieved from short term storage in the data storage device 540 of the determination device 122. In some embodiments, the historical data 742 is retrieved from the data storage device 740 of the database server 126. The historical data 742 may also be transmitted for use (e.g., transmitted and temporarily stored in in the data storage device 540 of the determination device 122).

At block 2704, the determination device 122 determines a total average number of units per procedure for the product. That is, the determination device 122 determines, for a specified period of time (e.g., one day, one week, one month, a quarter, or the like), how many total units of a particular product were used by a facility without factoring in the type of procedure, the personnel, the subject, and/or the like. The determination device 122 then determines the number of procedures in which the total units of a particular product were used for the same time period. The determination device then determines the total average number of units by dividing the total units by the number of procedures. For example, if 100 units were used in a time period and 20 procedures were performed, then the total average number of units per procedure would be 5 units per procedure (e.g., 100 units/20 procedures).

At block 2706, the determination device 122 provides the historical use data 546 and the determined total average number of units per procedure to a machine learning component. That is, the determination device 122 provides the data to an external machine learning server communicatively coupled to the determination device 122 or makes the data available for the purposes of operating one or more of the logic modules contained within the memory component 520, as described in greater detail herein. For example, the determination device 122 may utilize the network interface hardware 550 and/or the I/O hardware 530 to connect to an external machine learning server in embodiments where such a server is used such that the data can be transmitted to the external machine learning server.

At block 2708, the machine learning component generates a model based on various factors. That is, various factors that might affect a use of a particular product (e.g., a number of units of a particular product) may be considered for the purposes of determining a target number of units for the purposes of determining efficiency and pricing. As such, the model may be generated based on factors such as, but not limited to, a type of product used, the procedure for which the product was used, the personnel involved in using the product, certain characteristics of the subject upon which the procedure is performed, and/or the like. For example, if subjects having particular biometric or medical characteristics are prone to receive more units of a particular product due to those biometric or medical characteristics relative to other subjects, the machine learning component may consider this when determining a target number of units for the purposes of determining efficiency and pricing. The machine learning component that makes the determination according to block 2708 may be a machine learning server that is external to the determination device 122 and communicatively coupled to the determination device 122, or may be machine learning code contained within the determination device 122. For example, the machine learning component may be contained within the efficiency determination logic 523 and/or the pricing determination logic 524 of the memory component 520 of the determination device 122.

At block 2710, the machine learning component determines an expected number of units for a particular product using the model that was generated. That is, the machine learning component determines what an expected number of units of a particular product should be based on the various factors noted hereinabove with respect to block 2708. Accordingly, the determination of the expected number of units for a facility may vary based on the type of procedure being performed, the various personnel performing the procedure, certain characteristics of the subject on which the procedure was performed, and/or the like. In addition, since the model may be periodically updated as new information is received, the expected number of units may change over time as the model is fed with additional information. For example, as a physician becomes more proficient with using a particular type of product for a particular procedure, the number of units needed may decrease, thereby warranting a decrease in the expected number of units as determined by the machine learning component. It should be understood that the determination made according to block 2710 is generally completed for a plurality of products, and may further be completed for a plurality of different situations such that the determined pricing is narrowly tailored for a facility or even certain users in a facility For example, the determination made according to block 2710 may be made for each physician that uses the product in a facility such that pricing can be offered based on the physicians that use the product the most (e.g., pricing reflects weighted values based on physician use). The machine learning component that makes the determination according to block 2710 may be a machine learning server that is external to the determination device 122 and communicatively coupled to the determination device 122, or may be machine learning code contained within the determination device 122. For example, the machine learning component may be contained within the efficiency determination logic 523 of the memory component 520 of the determination device 122.

At block 2712, the machine learning component determines a best pricing tier amount based on the determined expected number. That is, the machine learning component determines a best pricing (e.g., a lowest possible pricing per procedure), given the determined expected number of units of a particular product. The pricing reflects a price per procedure that is paid if a particular procedure uses the expected number of units of a particular product. That is, if the determined number of units of a particular product for a particular procedure according to block 2710 is three units and the facility uses three units for a procedure (or averages three units per procedure over a previous period of time), the facility would receive the best pricing (e.g., lowest pricing) tier for that previous period of time, thereby resulting in a refund of any amount that was paid up front on a per-unit pricing scheme for the product that is over the best pricing per procedure, times the number of procedures, as described herein. In some embodiments, the pricing may be established in a manner so as to incentivize a facility that uses more than one unit per procedure to utilize per-procedure pricing. For example, if a facility averages two units per procedure, the pricing may be established such that the per-procedure price is greater than the per-unit price, but less than double the per-unit price such that the facility is guaranteed to save money at per-procedure pricing if more than one unit is used per procedure. In addition, since the model may be periodically updated as new information is received, the pricing may change over time as the model is fed with additional information. For example, as a physician becomes more proficient with using a particular type of product for a particular procedure, the number of units needed may decrease, thereby warranting a decrease in the expected number of units as determined by the machine learning component, which may warrant a change in price per procedure. The machine learning component that makes the determination according to block 2712 may be a machine learning server that is external to the determination device 122 and communicatively coupled to the determination device 122, or may be machine learning code contained within the determination device 122. For example, the machine learning component may be contained within the pricing determination logic 524 of the memory component 520 of the determination device 122.

In embodiments where a plurality of tiers of pricing are established, a determination may be made as to whether an additional pricing tier is necessary at block 2714. That is, if one tier has been established according to block 2712 and a plurality of tiers is to be established, the determination may be made that additional tiers are needed in the decision of block 2714. If additional pricing tiers are needed, the process proceeds to block 2716. If no other pricing tiers are needed (e.g., because a sufficient number of tiers has already been established), the process proceeds to block 2718.

At block 2716, additional pricing tiers are determined by the determination device 122. The additional pricing tiers may generally be pricing that is not as good as the best pricing tier determined at block 2712 (e.g., are at a higher cost per procedure than the best pricing tier). That is, if the best pricing tier established at block 2712 is $10 per procedure, another pricing tier may be established at a higher price than $10 per procedure (e.g., $15 per procedure, $20 per procedure, etc.). In some embodiments, pricing may be established at a predetermined interval that is greater than the best pricing tier established at block 2712 when establishing a next tier of pricing. For example, a predetermined interval may be $10 such that the next best tier after the best tier (e.g., the tier having the second lowest pricing) is $10 greater than the lowest price, a subsequent tier is $20 greater than the lowest price, and so on. In other embodiments, pricing may be established using machine learning whereby the pricing tiers are generated based on information that is provided to a machine learning component (e.g., an external machine learning server and/or machine learning code contained within the memory component 520 of the determination device 122). For example, information provided to a machine learning component may be usable by the machine learning component to predict a likelihood of a facility not meeting the expected number of units and setting a pricing accordingly. In some embodiments, the additional pricing tiers may be established to ensure that a facility does not become wasteful with products because of the per procedure cost. That is, the additional pricing tiers may allow for penalizing facilities that are unable to maintain efficiency of use of a particular product in accordance with the expected number of units. Once the additional pricing tier has been determined according to block 2716, the process may return to block 2714 for a determination as to whether additional pricing tiers are needed.

In some embodiments, pricing tiers may be given a label for users to more easily track which tier a particular pricing is. For example, in the embodiment depicted in FIG. 26, a best pricing (e.g., lowest pricing) may be "Emerald" pricing and a worst pricing (e.g., highest pricing) may be "Bronze" pricing, with varying degrees in between, such as "Platinum" pricing, "Gold" pricing, and "Silver" pricing. It should be understood that such labels are merely illustrative and the present disclosure is not limited any particular labeling.

Referring again to FIG. 27, if no additional pricing tiers are needed, the pricing tier amount(s) are provided by the determination device 122 to an external device. For example, the pricing tier amount(s) may be provided to the database server 126 for storage as the pricing data 744 such that the pricing data 744 can be accessed for the purposes of determining pricing when calculating a rebate due to a facility (if any), as described hereinbelow with respect to FIG. 28.

Figure 28:
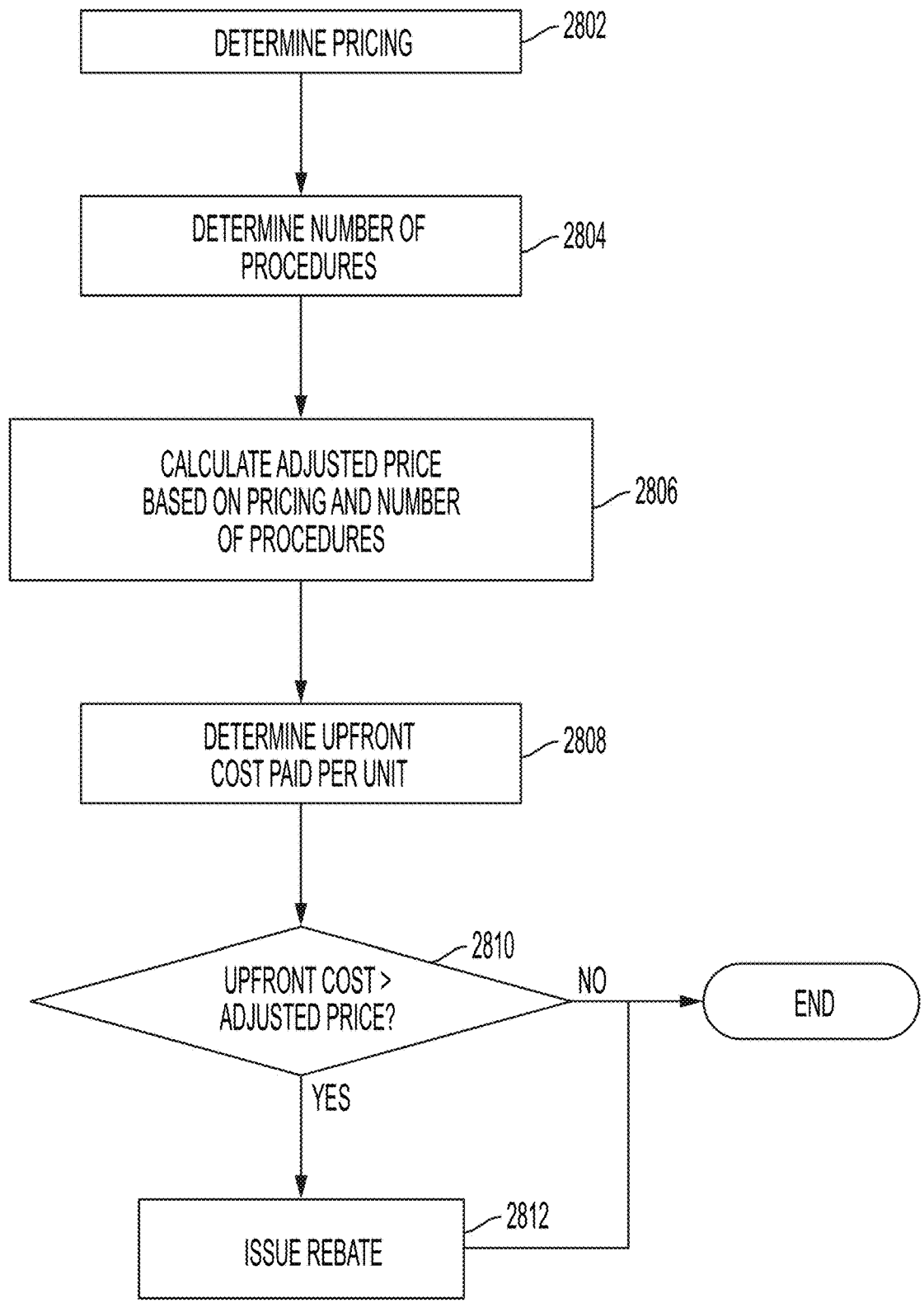
FIG. 28 schematically depicts a flow diagram of an illustrative method of determining a rebate according to one or more embodiments shown or described herein.

FIG. 28 depicts a flow diagram of an illustrative method of issuing a rebate, if any, based on the pricing determined according to the process depicted herein with respect to FIG. 27. Referring to FIGS. 5 and 28. The determination device 122 determines a pricing at block 2802. That is, referring also to FIG. 7, the determination device may retrieve the pricing data 744 and the associated efficiency, determine the appropriate tier to place the facility based on the determined expected use of a product and the actual use of a product.

At block 2804, the determination device 122 determines a number of procedures that have been completed over a predetermined time period. For example, if rebate checks are determined and issued quarterly, the determination step according to block 2804 may include determining a number of procedures a facility has performed over the past quarter.

At block 2806, the determination device 122 calculates an adjusted price based on the pricing and the number of procedures. That is, the determination device 122 multiplies the determined pricing by the number of procedures that used the particular product to obtain the adjusted price to be paid by the facility.

At block 2808, an upfront cost paid per unit is determined by the determination device 122. That is, the determination device 122 accesses data such as, for example, the historical data 742, the pricing data 744, and/or the other data 748 to determine how much was paid for the total number of units that were used over the same predetermined time period (e.g., the previous quarter, using the example from above).

A determination is made at block 2810 as to whether the upfront cost is greater than the adjusted price. That is, the determination device 122 compares the total price paid for all units used for a prior predetermined time period (e.g., the previous quarter, using the example from above) with the adjusted price calculated according to block 2806. If the upfront cost is not greater than the adjusted price, no further action is taken because no cost savings was realized by the facility. As such, the process ends. If the upfront cost is greater than the adjusted price, the process may move to block 2812.

At block 2812, a rebate is issued. That is, a monetary amount is paid to the facility, where the monetary amount represents the upfront cost minus the adjusted price. As such, the facility is ultimately paying the adjusted price because a rebate will be paid to make up for the difference in any overage observed due to the use of product on a per-procedure basis. The rebate may be issued by any means now known or later developed, including, but not limited to, an ACH transaction, a direct deposit, a wire transfer, issuance of a check, or the like.

It should now be understood that the systems, devices, and methods described herein determine a use of units of a product in a plurality of medical procedures and providing cost-per-procedure-like pricing after receiving a price-per-unit payment up front based on the determined use of units. One embodiment of a system includes a plurality of components in a facility monitoring system and a plurality of components in a product provider system, the facility monitoring system (and components thereof) being communicatively coupled to the product provider system (and components thereof) via a data gathering network. The components within the facility monitoring system include, but are not limited to, one or more data gathering devices, user interface device, and/or facility database server. The components within the product provider system include, but are not limited to, determination device, interface provider, and/or database server.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A system for providing per-procedure pricing for a product, the system comprising:
    a facility monitoring system comprising:
        one or more data gathering devices having one or more input/output hardware components and imaging device hardware, the one or more data gathering devices collecting data pertaining to use of a plurality of units of the product over a period of time via the one or more input/output hardware components and the imaging device hardware; and
    a product provider system communicatively coupled to the facility monitoring system, the product provider system comprising:
        a determination device that receives the data from the one or more data gathering devices and determines a total average number of units per procedure for the product, the determination device comprising a machine learning component trained to determine an expected number of units per procedure and determine a plurality of pricing tiers based on the determined expected number of units per procedure based on at least one of data pertaining to a number of units of the product, one or more types of procedures performed using the product, personnel that performed the one or more types of procedures, and subjects that received the one or more types of procedures and applies a weighting to the data pertaining to a number of units of the product, the one or more types of procedures performed using the product, the personnel that performed the one or more types of procedures, or the subjects that received the one or more types of procedures, wherein the weighting is used to determine the expected number of units per procedure;
        wherein the pricing tiers establishing a price that is used by the determination device to calculate an adjusted per-procedure price for the product over the period of time, the determination device issuing a rebate if the adjusted per-procedure price is less than an upfront cost paid.

2. The system of claim 1, wherein the facility monitoring system further comprises an interface provider comprising user interface hardware that displays an interface to a user, the interface containing information pertaining to the use of the plurality of units of the product over the period of time.

3. The system of claim 1, wherein the facility monitoring system further comprises a facility database server that comprises a data storage device storing the data pertaining to the use of the plurality of units of the product over the period of time.

4. The system of claim 1, wherein the product provider system further comprises an interface provider comprising input/output hardware that provides information pertaining to the expected number of units and the plurality of pricing tiers.

5. The system of claim 1, wherein the product provider system further comprises a database server that comprises a data storage device storing the data pertaining to the use of the plurality of units of the product over the period of time, information pertaining to the expected number of units, information pertaining to the plurality of pricing tiers, and information pertaining to the adjusted per-procedure price.

6. The system of claim 1, wherein:
a first pricing tier of the plurality of pricing tiers represents a lowest price provided when an efficiency of use indicates that an actual number of units used is equal to the expected number of units per procedure, and
a second pricing tier of the plurality of pricing tiers represents a highest price provided when the efficiency of use indicates that the actual number of units used is greater than the expected number of units per procedure.

7. The system of claim 1, wherein the upfront cost paid equals a number of units purchased times a price per unit.

8. A method of providing per-procedure pricing for a product by a determination device, the method comprising:
retrieving, by the determination device, historical use data for the product;
determining, by the determination device, a total average number of units per procedure for the product;
providing, by the determination device, the historical use data and the total average number of units per procedure to a machine learning component, wherein the machine learning component generates a model from the historical use data and the total average number of units per procedure and determines an expected number of units per procedure based on the model, based on at least one of data pertaining to a number of units of the product, one or more types of procedures performed using the product, personnel that performed the one or more types of procedures, and subjects that received the one or more types of procedures and applies a weighting to the data pertaining to a number of units of the product, the one or more types of procedures performed using the product, the personnel that performed the one or more types of procedures, or the subjects that received the one or more types of procedures, wherein the weighting is used to determine the expected number of units per procedure;
determining, by the determination device, a plurality of pricing tiers for the price per procedure based on the expected number of units per procedure;
determining, by the determination device, a per-procedure pricing to be offered from the plurality of pricing tiers based on a determined efficiency of use of the product, wherein the efficiency of use represents a closeness to the expected number of units per procedure;
calculating, by the determination device, an adjusted price to be paid based on the per-procedure pricing and a total number of procedures for a period of time; and
issuing, by the determination device, a rebate when a total upfront cost paid for all units on a per-unit basis is greater than the adjusted price to be paid, wherein the rebate represents a difference between the total upfront cost and the adjusted price to be paid.

9. The method of claim 8, wherein retrieving the historical use data comprises retrieving data pertaining to the number of units of the product, the one or more types of procedures performed using the product, the personnel that performed the one or more types of procedures, and the subjects that received the one or more types of procedures.

10. The method of claim 8, wherein:
a first pricing tier of the plurality of pricing tiers represents a lowest price provided when the efficiency of use indicates that an actual number of units used is equal to the expected number of units per procedure, and
a second pricing tier of the plurality of pricing tiers represents a highest price provided when the efficiency of use indicates that the actual number of units used is greater than the expected number of units per procedure.

11. The method of claim 8, wherein the total upfront cost paid on the per-unit basis equals a number of units purchased times a price per unit.

12. The method of claim 8, wherein providing the historical use data and the total average number of units per procedure to the machine learning component comprises providing the historical use data and the total average number of units per procedure to a remote machine learning server communicatively coupled to the determination device.

13. The method of claim 8, wherein the machine learning component is encoded in one or more software modules contained within a non-transitory memory component of the determination device.

14. The method of claim 8, further comprising storing the historical use data, information pertaining to the total average number of units per procedure, information pertaining to the expected number of units per procedure, the plurality of pricing tiers, and the per-procedure pricing on a data storage device.

15. The method of claim 8, wherein the model is continuously updated when additional historical use data is provided to the machine learning component.

16. A determination device that provides per-procedure pricing for a product, the determination device comprising:
a processing device; and
a non-transitory, processor readable storage medium communicatively coupled to the processing device, the non-transitory, processor readable storage medium comprising one or more programming instructions thereon that, when executed, cause the processing device to:
retrieve historical use data for the product,
determine a total average number of units per procedure for the product;
provide the historical use data and the total average number of units per procedure to a machine learning component, wherein the machine learning component generates a model from the historical use data and the total average number of units per procedure and determines an expected number of units per procedure based on the model, based on at least one of data pertaining to a number of units of the product, one or more types of procedures performed using the product, personnel that performed the one or more types of procedures, and subjects that received the one or more types of procedures and applies a weighting to the data pertaining to a number of units of the product, the one or more types of procedures performed using the product, the personnel that performed the one or more types of procedures, or the subjects that received the one or more types of procedures, wherein the weighting is used to determine the expected number of units per procedure, determine a plurality of pricing tiers for the price per procedure based on the expected number of units per procedure, determine a per-procedure pricing to be offered from the plurality of pricing tiers based on a determined efficiency of use of the product, wherein the efficiency of use represents a closeness to the expected number of units per procedure, calculate an adjusted price to be paid based on the per-procedure pricing and a total number of procedures for a period of time, and issue a rebate when a total upfront cost paid for all units on a per-unit basis is greater than the adjusted price to be paid, wherein the rebate represents a difference between the total upfront cost and the adjusted price to be paid.

17. The determination device of claim 16, wherein the programming instruction that, when executed, cause the processing device to retrieve the historical use data further cause the processing device to retrieve data pertaining to the number of units of the product, the one or more types of procedures performed using the product, the personnel that performed the one or more types of procedures, and the subjects that received the one or more types of procedures.

18. The determination device of claim 16, wherein:
- a first pricing tier of the plurality of pricing tiers represents a lowest price provided when the efficiency of use indicates that an actual number of units used is equal to the expected number of units per procedure, and
- a second pricing tier of the plurality of pricing tiers represents a highest price provided when the efficiency of use indicates that the actual number of units used is greater than the expected number of units per procedure.

19. The determination device of claim 16, wherein the programming instructions that, when executed, cause the processing device to provide the historical use data and the total average number of units per procedure to the machine learning component further cause the processing device to provide the historical use data and the total average number of units per procedure to a remote machine learning server communicatively coupled to the determination device.

20. The determination device of claim 16, wherein the model is continuously updated when additional historical use data is provided to the machine learning component.

* * * * *